(12) United States Patent
Hall et al.

(10) Patent No.: US 6,395,541 B1
(45) Date of Patent: *May 28, 2002

(54) METHODS FOR THE IDENTIFICATION OF COMPOUNDS CAPABLE OF INHIBITING HIV-1 VIRAL REPLICATION EMPLOYING MURINE CELL LINES EXPRESSING HUMAN TOPOISOMERASE I

(75) Inventors: William W. Hall, New York, NY (US); Hidehiro Takahashi, Tokyo (JP)

(73) Assignee: The Rockefeller University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/814,866

(22) Filed: Mar. 11, 1997

Related U.S. Application Data

(63) Continuation of application No. 08/652,074, filed on May 23, 1996, now abandoned.

(51) Int. Cl.$^7$ .................................................. C12N 5/06
(52) U.S. Cl. ..................................... 435/354; 424/188.1
(58) Field of Search ........................... 425/5, 2.21, 2.24, 425/69.1, 172.3, 325; 424/188.1, 352–354

(56) References Cited

U.S. PATENT DOCUMENTS

| | | |
|---|---|---|
| 4,604,463 A | 8/1986 | Miyasaka et al. |
| 5,004,758 A | 4/1991 | Boehm et al. |
| 5,064,823 A | 11/1991 | Lee et al. |
| 5,141,867 A | 8/1992 | Ivanoff et al. |
| 5,244,903 A | 9/1993 | Wall et al. |
| 5,317,009 A | 5/1994 | Lee-Huang et al. |
| 5,364,858 A | 11/1994 | Wall et al. |
| 5,422,344 A | 6/1995 | Priel et al. |
| 5,496,830 A | 3/1996 | Shapiro et al. |
| 5,559,235 A | 9/1996 | Luzzio et al. |

FOREIGN PATENT DOCUMENTS

| | | |
|---|---|---|
| WO | WO 90/07119 | 6/1990 |
| WO | WO 91/09872 | 7/1991 |
| WO | WO 92/14470 | 9/1992 |
| WO | WO 92/20813 | 11/1992 |
| WO | WO 92/22654 | 12/1992 |
| WO | WO 94/04160 | 3/1994 |
| WO | WO 95/09169 | 4/1995 |
| WO | WO 96/38449 | 12/1996 |

OTHER PUBLICATIONS

Houdebine, L–M., 1994, "Production of pharmaceutical proteins from transgenic animals.", J. Biotech. 34:269–287.*

Wall, R.J., 1996, "Transgenic livestock: Progress and prospects for the future.", Theriogenol. 45:57–68.*

Kappel, C.A., et al., 1992, "Regulating gene expression in transgenic animals.", Curr. Opin. Biotech. 3:548–553.*

D'Arpa et al., 1988, "cDNA cloning of human DNA topoisomerase I: catalytic activity of 67.7–kDa carboxyl–terminal fragment", Proc. Natl. Acad. Sci. USA 85:2543–2547.*

Kunze et al., 1991, "Structure of the human type I DNA topoisomerase gene", J. Biol. Chem. 266:9610–9616.*

Gillespie et al., 1993, "Tissue–specific expression of human CD4 in transgenic mice", Molec. Cell. Biol. 13:2952–2958.*

Lorés et al., 1992, "Expression of human CD4 in transgenic mice does not confer sensitivity to human immunodeficiency virus infection", AIDS Res. Human Retro. 8:2063–2071.*

Brady et al., 1994, "Transgenic mice as models of human immunodeficiency virus expression and related cellular effects", J. Gen. Virol. 75:2549–2558.*

Jardine et al., "Cellular topoisomerase I activity associated with HIV–1", AIDS Res. Human Retro. 9:1245–1250.*

Takahashi et al., 1995, "Human immunodeficiency virus type 1 reverse transcriptase: enhancement of activity by interaction with cellular topoisomerase I", Proc. Natl. Acad. Sci. USA 92:5694–5698.*

Miller et al., 1993, "Use of retroviral vectors for gene transfer and expression", Meth. Enzymol. 217:581–599.*

Moulton et al., 1998, "9–Nitrocamptothecin Inhibits Tumor Necrosis Factor–Mediated Activation of Human Immunodeficiency Virus Type 1 and Enhances Apoptosis in a Latently Infected T Cell Clone", AIDS Res. and Human Retroviruses 14:39–49.

Horiguchi et al., 1996, "TAN–1609 (Herboxidien): A Microbial Polyketide Which Blocks the Cell–Cycle at $G_2$ Phase in Human and Murine Tumor Cells", J. Takeda Res. Labs 55:149–159.

Ho et al., "Rapid Turnover of Plasma Virons and CD4 Lymphocytes in HIV–1 Infection", Nature 373:123–126.

(List continued on next page.)

Primary Examiner—Laurie Scheiner
Assistant Examiner—Jeffrey S. Parkin
(74) Attorney, Agent, or Firm—Pennie & Edmonds LLP

(57) ABSTRACT

The present invention relates to therapeutic protocols and pharmaceutical compositions designed to target topo I for the treatment of HIV infection. The invention relates to therapeutic modalities and pharmaceutical compositions for the treatment of HIV-infection using human topo I and its interaction with HIV gag and RT as a target for intervention. The invention further relates to the use of human topo I to enhance the activity of RT. The present invention also relates to the expression of human topo I in transgenic animals, in particular mice, as a system to study the HIV life cycle and to screen agents for their ability to interfere with the HIV life cycle.

4 Claims, 16 Drawing Sheets

OTHER PUBLICATIONS

Figure 2:
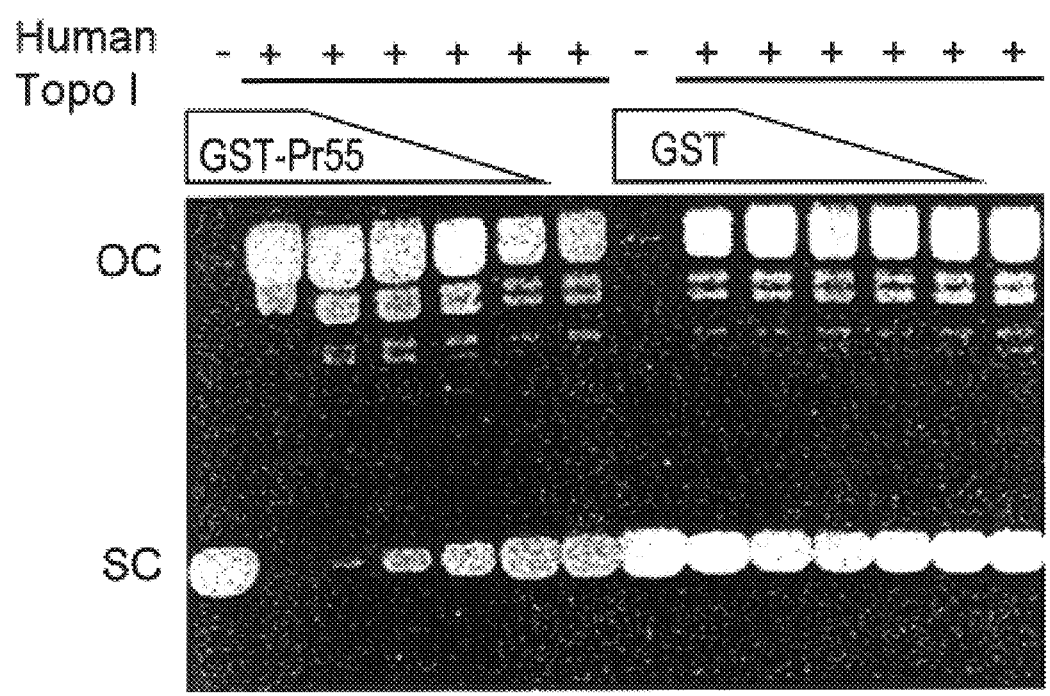

Horiguchi and Tanida, 1995, "Rescue of *Schizosaccharomyces pombe* from Camptothecin–Mediated Death by a DNA Topoisomerase I Inhibitor, TAN–1518 A", Biochem. Pharmacol. 49:1395–1401.

Rice et al., 1995, "Inhibitors of HIV Nucleocapsid Protein Zinc Fingers as Candidates for the Treatment of AIDS", Science 270:1194–1197.

Wargnier et al., 1995, "Identification of Human Granzyme B Promoter Regulatory Elements Interacting with Activated T–Cell–Specific Proteins: Implication of Ikaros and CBF Binding Sites in Promoter Activation", Mol. Cell. Biol. 92:6930–6934.

Funabashi et al., 1994, "TAN–1496 A, C, and E, Diketopiperazine Antibiotics with Inhibitory Activity Against Mammalian DNA Topoisomerase I", J. Antibiotics 47:1202–1218.

Broder et al., 1993, "The Block HIV–1 Envelope Glycoprotein–Mediated Membrane Fusion in Animal Cells Expressing Human CD4 Can Be Overcome by a Human Cell Component(s)", Virol. 193:483–491.

Rossi, 1994, "Making Ribozymes Work in Cells", Curr. Biol. 4:469–471.

Kawanishi, 1993, "Topoisomerase I and II Activities are Required for Epstein–Barr Virus Replication", J. Gen. Virol. 74:2263–2268.

Weiss et al., 1992, "Recombinant HIV–1 Nucleocapsid Protein p15 Produced as a Fusion Protein with Glutathione S–Transferase in *Escherichia coli* Mediates Dimerization and Enhances Reverse Transcription of Retroviral RNA", Gene 121:203–212.

Hoshikawa et al., 1991, "Role of the gag and pol Genes of Human Immunodeficiency Virus in the Morphogenesis and Maturation of Retrovirus–Like Particles Expressed by Recombinant Vaccinia Virus: and Ultrastructural Study", J. Gen. Virol. 72:2509–2517.

Mitsuya et al., 1991, "Targeted Therapy of Human Immunodeficiency Virus–Related Disease", FASEB J. 5:2369–2381.

Civitico et al., 1990, "Antiviral Strategies in Chronic Hepatitis B Virus Infection: II. Inhibition of Duck Hepatitis B Virus In Vitro Using Conventional Antiviral Agents and Supercoiled–DNA Active Compounds", J. Med. Virol. 31:90–97.

Daar et al., 1990, "High Concentrations of Recombinant Soluble CD4 are Required to Neutralize Primary Human Immunodeficiency Virus Type 1 Isolates", Proc. Natl. Acad. Sci. USA 87:6574–6578.

Erickson et al., 1990, "Design, Activity and 2.8 Å Crystal Structural of a $C_2$ Symmetric Inhibitor Complexed to HIV–1 Protease", Science 249:527–533.

Kahn et al., 1990, "The Safety and Pharmacokinetics of Recombinant Soluble CD4 (rCD4) in Subjects with the Acquired Immunodeficiency Syndrome (AIDS) and AIDS–Related Complex", Ann. Internal Med. 112:254–261.

Mitsuya et al., 1990, "Molecular Targets for AIDS Therapy", Science 249:1533–1544.

Priel et al., 1990, "Topoisomerase I Activity Associated with Human Immunodeficiency Virus (HIV) Particles and Equine Infectious Anemia Virus Core", EMBO J. 9:4167–4172.

Schaak et al., 1990, "Transcription of Adenovirus and HeLa Cell Genes in the Presence of Drugs that Inhibit Topoisomerase I and II Function", Nucl. Acids Res. 18:1499–1508.

Schooley et al., 1990, "Recombinant Soluble CD4 Therapy in Patients with the Acquired Immunodeficiency Syndrome (AIDS) and AIDS–Related Complex", Ann. Internal Med. 112:247–253.

Stewart et al., 1990, "Rapid Induction of c–fos Transcription Reveals Quantitative Linkage of RNA Polymerase II and DNA Topoisomerase I Enzyme Activities", Cell 60:141–149.

Wong and Hsu, 1990, "Involvement of Topoisomerase in Replication, Transcription, and Packaging of the Linear Adenovirus Genome", J. Virol. 64:691–699.

Yasuda et al., 1990, "Induction of Protective Immunity in Animals Vaccinated with Recombinant Vaccinia Viruses that Express PreM and E Glycoproteins of Japanese Encepthalitis Virus", J. Virol. 64:2788–2795.

Fujiwara et al., 1989, "Integration of Mini–Retroviral DNA: A Cell–Free Reaction for Biochemical Analysis of Retroviral Integration", Proc. Natl. Acad. Sci. USA 86:3065–3069.

Giovanella et al., 1989, "DNA Topoisomerase I–Targeted Chemotherapy of Human Colon Cancer in Xenografts", Science 246:1046–1048.

Jaxel et al., 1989, "Structure–Activity Study of the Actions of Camptothecin Derivatives on Mammalian Topoisomerase I: Evidence for a Specific Receptor Site and a Relation to Antitumor Activity", Cancer Res. 49:1465–1469.

Larder et al., 1989, "HIV with Reduced Sensitivity to Zidovudine (AZT) Isolated During Prolonged Therapy", Science 243:1731–1734.

Priel et al., 1989, "Detection of a Novel DNA Topoisomerase Activity Associated with Human Immunodeficiency Virus (HIV) and Other Retrovirus Particles", Proc. $V^{th}$ Int'l. Conf. on AIDS, p. 586.

Yarchoan et al., 1989, "Phase I Study of the Administration of Recombinant Soluble CD5 (rCD4) by Continuous Infusion to Patients with AIDS or ARC", Proc. $V^{th}$ Int'l. Conf. on AIDS, p. 564.

Pottage et al., 1988, "Treatment of Human Immunodeficiency Virus–Related Thrombocytopenia with Zidovudine", JAMA 260:3045–3048.

Willey et al., 1988, "In Vitro Mutagenesis Identifies a Region Within the Envelope Gene of the Human Immunodeficiency Virus that is Critical for Infectivity", J. Virol. 62:139–147.

Fischl et al., 1987, "The Efficacy of Azidothymidine (AZT) in the Treatment of Patients with AIDS and AIDS–Related Complex", New Eng. J. Med. 317:185–191.

Mitsuya and Broder, 1987, "Strategies for Antiviral Therapy in AIDS", Nature 325:773–778.

Smith et al., 1987, "Blocking of HIV–1 Infectivity by a Soluble, Secreted Form of the CD4 Antigen", Science 238:1704–1707.

Maddon et al., 1986, "The T4 Gene Encodes the AIDS Virus Receptor and is Expressed in the Immune System and the Brain", Cell 47:333–348.

McDougal et al., 1986, "Binding of HTLV–III/LAV to T4$^+$ Cells by a Complex of the 110K Viral Protein and the T4 Molecule", Science 231:382–385.

Pinter et al., 1986, "Ecotropic Murine Leukemia Virus–Induced Fusion of Murine Cells", J. Virol. 57:1048–1054.

Snapka, 1986, "Topoisomerase Inhibitors Can Selectively Interfere with Different Stages of Simian Virus 40 DNA Replication" Mol. Cell. Biol. 6:4221–4227.

Barin et al., 1985, "Virus Envelope Protein of HTLV–III Represents Major Target Antigen for Antibodies in AIDS Patients", Science 228:1094–1096.

Ratner et al., 1985, "Complete Nucleotide Sequence of the AIDS Virus, HTLV–III", Nature 313:277–284.

Dalgliesh et al., 1984, "The CD4 (T4) Antigen is an Essential Component of the Receptor for the AIDS Retrovirus", Nature 312:763–767.

Klatzmann et al., 1984, "T–Lymphocyte T4 Molecule Behaves as the Receptor for Human Retrovirus LAV", Nature 312:767–768.

Goff et al., 1981, "Isolation and Properties of Moloney Murine Leukemia Virus Mutants: Use of a Rapid Assay for Release of Virion Reverse Transcriptase", J. Virol. 38:239–248.

Donis–Keller et al., 1980, "Nucleotide Sequences Associated with Differences in Electrophoretic Mobility of Envelope Glycoprotein gp70 and with $G_{IX}$ Antigen Phenotype of Certain Murine Leukemia Viruses", Proc. Natl. Acad. Sci USA 77:1642–1645.

* cited by examiner

FIG. 1

ORIGIN
          1 gtggcttggt gcaagaagtg gggtgtccaa ttgagaagat ttacaacaaa acccagcgga
         61 gaagtttgcc tgggccattg acatggctga tgaagactat gagttttagc cagtctcaag
        121 aggcagagtt ctgtgaagag gaacagtgtg gtttgggaaa gatggataaa ctgagcctca
        181 cttgccctcg tgcctcgggg agagaggcag caagtcttaa caaaccaaca tctttgcgaa
        241 aagataaagc ctggagatat tataagggag agctgagcca att

FIG.11

METHODS FOR THE IDENTIFICATION OF COMPOUNDS CAPABLE OF INHIBITING HIV-1 VIRAL REPLICATION EMPLOYING MURINE CELL LINES EXPRESSING HUMAN TOPOISOMERASE I

This is a continuation, of application Ser. No. 08/652,074, filed May 23, 1996, now abandoned.

1. INTRODUCTION

The present invention relates to therapeutic protocols and pharmaceutical compositions designed to target topoisomerase I (topo I) as a treatment for HIV-infection. In a preferred embodiment, the present invention relates to therapeutic protocols designed to interfere with the interaction of topo I with the HIV proteins gag and reverse transcriptase (RT), as a treatment for HIV-infection. The present invention still further relates to transgenic animals which express human topo I, in particular transgenic mice, and their use as a system to screen agents for their ability to interfere with the HIV life cycle.

2. BACKGROUND OF THE INVENTION

2.1. The Human Immunodeficiency Virus

The human immunodeficiency virus (HIV) has been implicated as the primary cause of the slowly degenerative immune system disease termed acquired immune deficiency syndrome (AIDS) (Barre-Sinoussi, F. et al., 1983, Science 220:868–870; Gallo, R. et al., 1984, Science 224:500–503). There are at least two distinct types of HIV: HIV-1 (Barre-Sinoussi, F. et al., 1983, Science 220:868–870; Gallo R. et al., 1984, Science 224:500–503) and HIV-2 (Clavel, F. et al., 1986, Science 233:343–346; Guyader, M. et al., 1987, Nature 326:662–669). Further, a large amount of genetic heterogeneity exists within populations of each of these types. In humans, HIV replication occurs prominently in $CD4^+$ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich, N. et al., 1984, RNA Tumor Viruses, Weiss, R. et al., eds., CSH-Press, pp. 949–956). Retroviruses are small enveloped viruses that contain a single-stranded RNA genome, and replicate via a DNA intermediate produced by a virally-encoded reverse transcriptase, an RNA-dependent DNA polymerase (Varmus, H., 1988, Science 240:1427–1439). Other retroviruses include, for example, oncogenic viruses such as human T cell leukemia viruses (HTLV-I,-II,-III), and feline leukemia virus.

The HIV viral particle comprises a viral core, composed in part of capsid proteins, together with the viral RNA genome and those enzymes required for early replicative events. Myristylated Gag protein forms an outer shell around the viral core, which is, in turn, surrounded by a lipid membrane envelope derived from the infected cell membrane. The HIV envelope surface glycoproteins are synthesized as a single 160 Kd precursor protein which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammarskjold, M. & Rekosh, D., 1989, Biochem. Biophys. Acta 989:269–280).

HIV is targeted to $CD4^+$ cells because a CD4 cell surface protein (CD4) acts as the cellular receptor for the HIV-1 virus (Dalgleish, A. et al., 1984, Nature 312:763–767; Klatzmann et al., 1984, Nature 312:767–768; Maddon et al., 1986, Cell 47:333–348). Viral entry into cells is dependent upon gp120 binding the cellular CD4 receptor molecules (McDougal, J. S. et al., 1986, Science 231:382–385; Maddon, P. J. et al., 1986, Cell 47:333–348), explaining HIV's tropism for $CD4^+$ cells, while gp41 anchors the envelope glycoprotein complex in the viral membrane. While these virus:cell interactions are necessary for infection, there is evidence that additional virus:cell interactions are also required.

Purified HIV virions have been reported to have topoisomerase activity (Priel et al., 1990, EMBO J. 9:4167–4172). Topoisomerase I is an enzyme that modifies the topological state of the DNA by breakage and rejoining of single DNA strands and relaxing both positive and negative supercoils. In addition to playing a role in normal cell function, topo I of cellular origin has also been shown to be involved in the replication of a number of DNA viruses, where it has been associated with DNA replication, transcription, and integration (Wang et al. 1990, J. Virol. 64:691–699; Shaack et al., 1990, Nucleic Acids Research 18:1499–1508; Kawanishi 1993, J. Gen. Virology 74:2263–2268). It has been suggested that the topo I activity associated with HIV virions is viral in origin in that it differs from cellular topo I in its requirements for optimal enzyme activity (Priel et al., 1990, EMBO J. 9:4167–4172).

2.2. HIV Treatment

HIV infection is pandemic and HIV-associated diseases represent a major world health problem. Although considerable effort is being put into the design of effective therapeutics, currently no curative anti-retroviral drugs against AIDS exist. In attempts to develop such drugs, several stages of the HIV life cycle have been considered as targets for therapeutic intervention (Mitsuya, H. et al., 1991, FASEB J. 5:2369–2381). Many viral targets for intervention with HIV life cycle have been suggested, as the prevailing view is that interference with a host cell protein would have deleterious side effects. For example, virally encoded reverse transcriptase has been one focus of drug development. A number of reverse-transcriptase-targeted drugs, including 2',3'-dideoxynucleoside analogs such as AZT, ddI, ddC, and d4T have been developed which have been shown to been active against HIV (Mitsuya, H. et al., 1991, Science 249:1533–1544). While beneficial, these nucleoside analogs are not curative, probably due to the rapid appearance of drug resistant HIV mutants (Lander, B. et al., 1989, Science 243:1731–1734). In addition, the drugs often cause toxic side effects such as bone marrow suppression, vomiting, and liver function abnormalities.

Attempts are also being made to develop drugs which can inhibit viral entry into the cell, the earliest stage of HIV infection. Here, the focus has thus far been on CD4, the cell surface receptor for HIV. Recombinant soluble CD4, for example, has been shown to inhibit infection of $CD4^+$ T cells by some HIV-1 strains (Smith, D. H. et al., 1987, Science 238:1704–1707). Certain primary HIV-1 isolates, however, are relatively less sensitive to inhibition by recombinant CD4 (Daar, E. et al., 1990, Proc. Natl. Acad. Sci. USA 87:6574–6579). In addition, recombinant soluble CD4 clinical trials have produced inconclusive results (Schooley, R. et al., 1990, Ann. Int. Med. 112:247–253; Kahn, J. O. et al., 1990, Ann. Int. Med. 112:254–261; Yarchoan, R. et al., 1989, Proc. Vth Int. Conf. on AIDS, p. 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, Science 249:527–533). The clinical outcome of these candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin, et al., 1985, Science 228:1094–1096). Thus far, therefore, these proteins seem to be the most promising candidates to act as antigens for anti-HIV vaccine development. Several groups have begun to use various portions of gp160, gp120, and/or gp41 as immunogenic targets for the host immune system. See for example, Ivanoff, L. et al., U.S. Pat. No. 5,141,867; Saith, G. et al., WO 92/22,654; Shafferman, A., WO 91/09,872; Formoso, C. et al., WO 90/07,119. To this end, vaccines directed against HIV proteins are problematic in that the virus mutates rapidly rendering many of these vaccines ineffective. Clinical results concerning these candidate vaccines, however, still remain far in the future.

Thus, although a great deal of effort is being directed to the design and testing of anti-retroviral drugs, effective, non-toxic treatments are still needed.

3. SUMMARY OF THE INVENTION

The present invention relates to therapeutic protocols and pharmaceutical compositions designed to target topo I for the treatment of HIV infection. The invention relates to therapeutic modalities and pharmaceutical compositions for the treatment of HIV-infection using human topo I and its interaction with HIV gag and RT as a target for intervention.

The present invention relates to animal cell lines expressing human topo I, in particular mouse cell lines, and their use as a system to study the HIV life cycle and screen agents for their ability to interfere with the HIV life cycle. The present invention also relates to human topo I transgenic animals, in particular mice, and their use as a system to study the HIV life cycle and to screen agents for their ability to interfere with the HIV life cycle.

The invention is based, in part, on the Applicants' surprising discoveries that (1) human topo I interacts with and is activated by HIV gag in a species specific manner; (2) the interaction between human topo I and gag is required to enhance HIV RT activity; and (3) the interactions between human topo I and HIV gag and RT are required to support HIV replication. This model is based on the Applicants' observation that murine cells expressing human CD4 are not able to support HIV replication. However, murine cells support HIV replication. The expression of human topo I was also shown to enhance the activity of HIV RT in murine cells.

That human topo I interacts with and is activated by HIV gag, and that this complex is required for activation of HIV RT is further supported by the working examples described infra which demonstrate (1) that gag proteins activate cellular topo I and immunoprecipitated-gag proteins induce topo I activity in a species specific manner; (2) mouse cells expressing both human CD4 and topo I infected with HIV effectively reverse transcribe the HIV RNA genome; and (3) the topo I inhibitor, TAN134A, which attacks the topo I site directly, inhibits HIV RT activity in murine cells.

The invention further relates to a murine model for HIV replication, in which transgenic mice expressing both the human CD4 cell surface protein and human topo I are able to support HIV-1 replication. The present invention also encompasses a murine model for HIV replication, in which transgenic mice express human topo I and a HIV pseudovirus is used to infect the animals. The HIV pseudovirus may contain an envelope protein from a virus with a natural tropism for murine cells, such as the murine leukemia virus, which bypasses internalization of the HIV virus by the murine cells. These transgenic mice have utility to screen for other host cellular components required to support the HIV life cycle (i.e., entry, replication and assembly), in addition to screen for drugs and compounds which may have anti-HIV activity.

The invention relates to various modalities of treatment for HIV infection based on the proposed model. The invention further relates to the use of the murine HIV model system for screening test compounds, such as drugs, ligands (natural or synthetic), proteins, peptides and small organic molecules for their ability to interfere with the interaction between human topo I and HIV gag and RT.

The present invention further relates to the use of such identified inhibitors in pharmaceutical compositions designed to inhibit human topo I and/or the interaction between human topo I and HIV gag and/or HIV RT for the treatment and/or prevention of HIV infection. The present invention further encompasses the preparation of such pharmaceutical compositions for the treatment and/or prevention of HIV infection.

The invention also encompasses combinations of a topoisomerase I inhibitor with a least one other antiviral having a different site of action than the viral replication inhibitor. Such a combination provides an improved therapy based on the dual action of these therapeutics whether the combination is synergistic or additive.

3.1. Definitions

As used herein, the term "topoisomerase I" or "topo I" refers to the protein topoisomerase I which has the activity of modifying the topological state of DNA, and any derivative of topo I thereof, or fragments or peptides having an amino acid sequence corresponding to topo I.

As used herein, the term "HIV pseudovirus" refers to a HIV virus that expresses a coat proten or an envelope protein which renders the virus capable of infecting a mouse cell. An example of such a protein is the envelope protein of the murine leukemia virus.

As used herein, the term "to target" means to inhibit, block, or prevent gene expression, enzymatic activity, or interaction with other cellular or viral factors.

As used herein, the term "treating or preventing HIV infection" means to inhibit the replication of the HIV virus, to inhibit HIV transmission, or to prevent HIV from establishing itself in its host, and to ameliorate or alleviate the symptoms of the disease caused by HIV infection. The treatment is considered therapeutic if there is a reduction in viral load, decrease in mortality and/or morbidity.

As used herein, the term "pharmaceutically acceptable carrier" refers to a carrier medium that does not interfere with the effectiveness of the biological activity of the active ingredient, is chemically inert and is not toxic to the patient to whom it is administered.

The term "therapeutic agent" refers to any molecule compound or treatment, preferably an antiviral, that assists in the treatment of a viral infection or the diseases caused thereby.

4. BRIEF DESCRIPTION OF THE DRAWINGS

Figure 1:
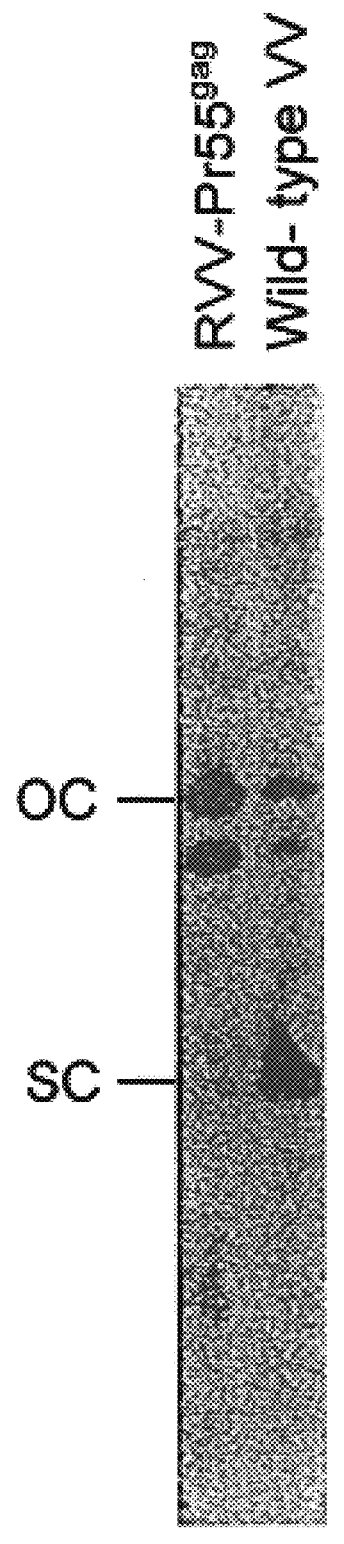

FIG. 1. Southern hybridization analysis of transfected supercoiled plasmid DNA in HeLa cells infected with RVV expressing HIV Pr55gag (RVV-Pr55gag) or wild-type vaccinia virus (wild-type VV). OC refers to open circle and relaxed DNA, and SC refers to supercoiled DNA.

FIG. 2. Topo I activity after the interactions of human topo I with GST-Pr55gag or GST alone. Five-tenths microgram of supercoiled plasmid DNA was incubated with 0.1 unit of human topo I and GST-Pr55gag or GST alone at final concentrations of 50, 10, 2, 0.4, 0.08 µg/ml (+) for 20 minutes at 37° C. Reactions without human topo I are indicated (−). Products were analyzed by electrophoresis on 1% agarose gels.

Figure 3A:
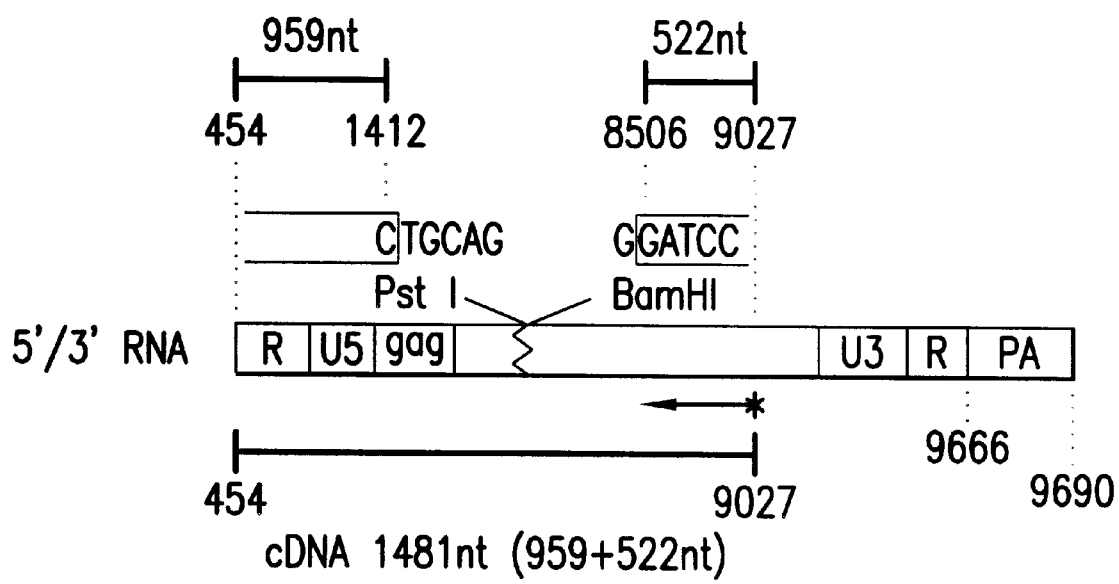
Figure 3B:
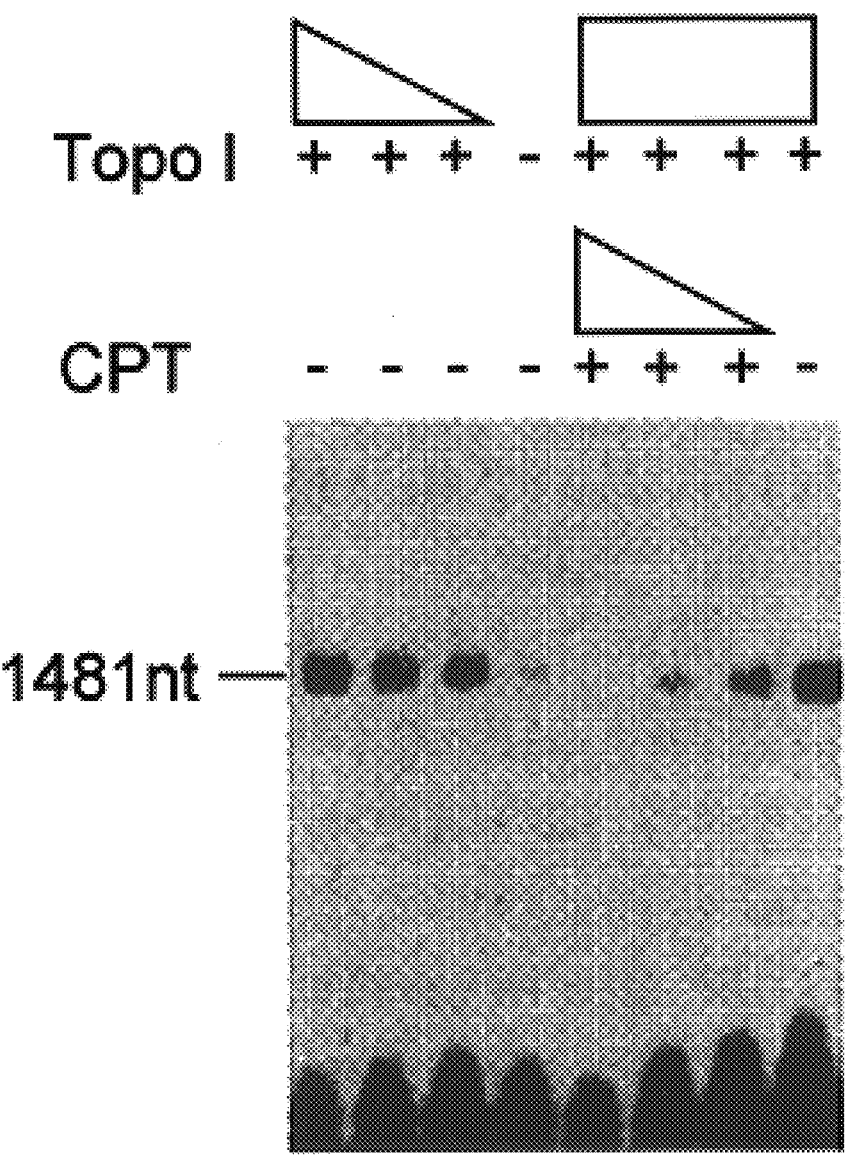

FIG. 3. Influence of cellular topo I on HIV-1 RT activity. FIG. 3A. Schematic representation of the RNA template employed in the RT assays. The 5'/3'RNA contains the 5'R, U5, and part of the gag region truncated to the nef gene and the 3'U3, and poly(A) tail (PA). An end-labeled primer (*) was employed to initiate cDNA synthesis and would be expected to result in a product of 1481 nucleotides (nt). FIG. 3B. Phosphorescence image analysis of cDNA products following agarose gel electrophoresis. The presence or absence of topo I is indicated by + and −, respectively. Similarly the presence or absence of CPT is indicated by + and −.

Figure 4A:
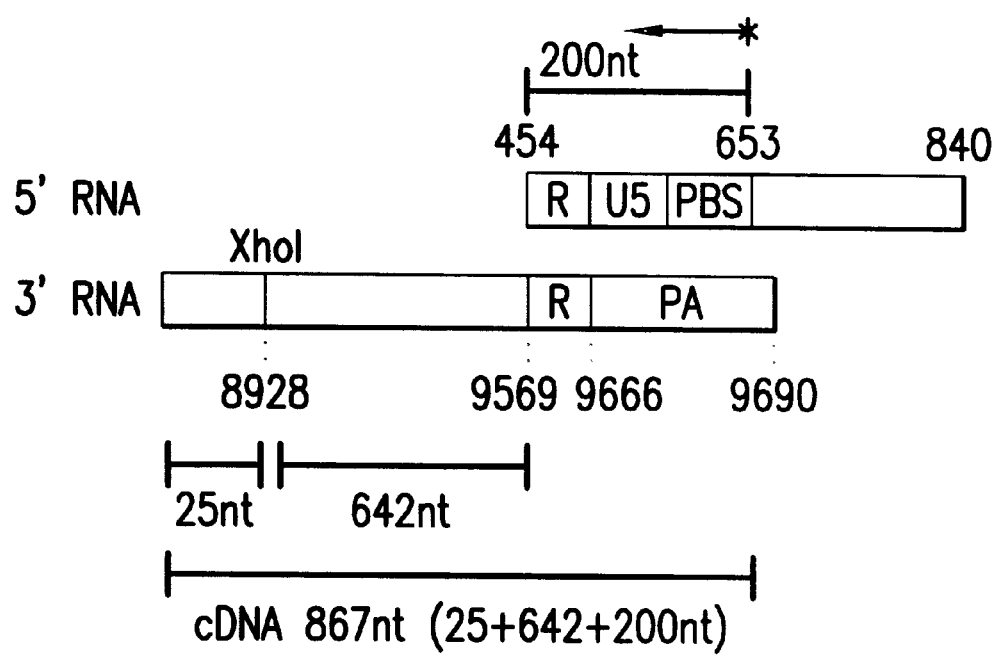
Figure 4B:
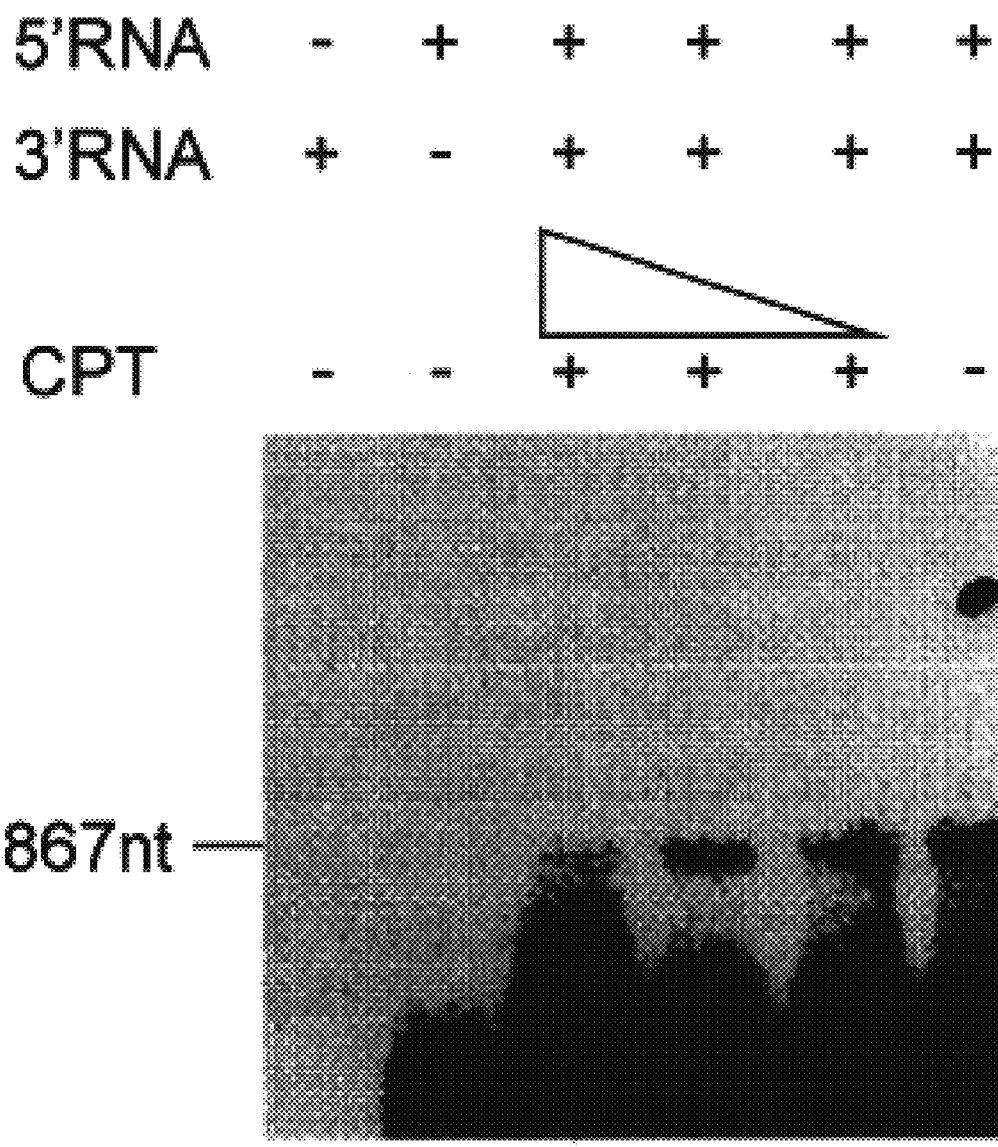

FIG. 4. Analysis of ssDNA synthesis and strand transfer. FIG. 4A. Schematic representation of two RNA templates employed. The 5'RNA represents the 5'end of HIV-1 RNA and contains the R, U5, and PBS. The 3'RNA represents the 3'end of the HIV-1 RNA and contains the R region and the poly(A) tail. ssDNA synthesis was initiated by an end labeled primer (*) corresponding to the primer binding site (PBS) in the 5'RNA. After strand transfer to the 3'RNA, this would be expected to result in a cDNA product of 867 nucleotides. FIG. 4B. Phosphorescence image analysis of the cDNA product after agarose gel electrophoresis. The presence and absence of 5'RNA and 3'RNA templates are indicated by + and −, respectively. The effects of CPT at concentrations of 400, 40 and 4 µM are indicated by +. Topo I was used at the final concentration of 0.16 unit per 50 µl in all experiments.

Figure 5:
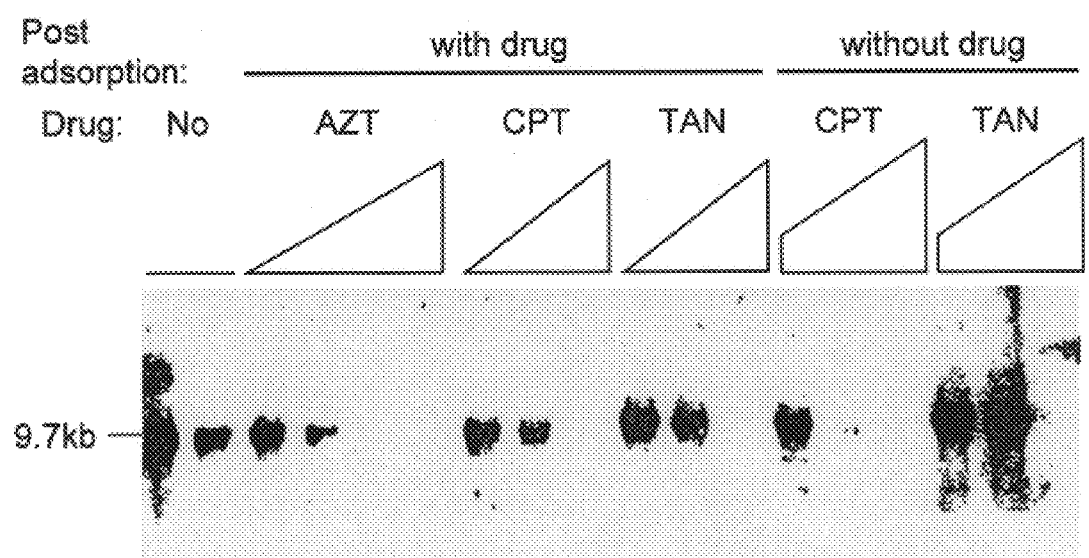

FIG. 5. Southern hybridization of DNA from HIV-1 infected cells with drug treatment. Mouse cells, MT2, infected with the HIV-1 IIIB strain were treated with AZT, CPT or TAN at concentrations (from right to left) AZT 0.01, 0.1, 1.0, 10 µg/ml, CPT 0.01, 0.1, 1.0 µg/ml, TAN 0.01, 0.1, 1.0 µg/ml respectively.

Figure 6:
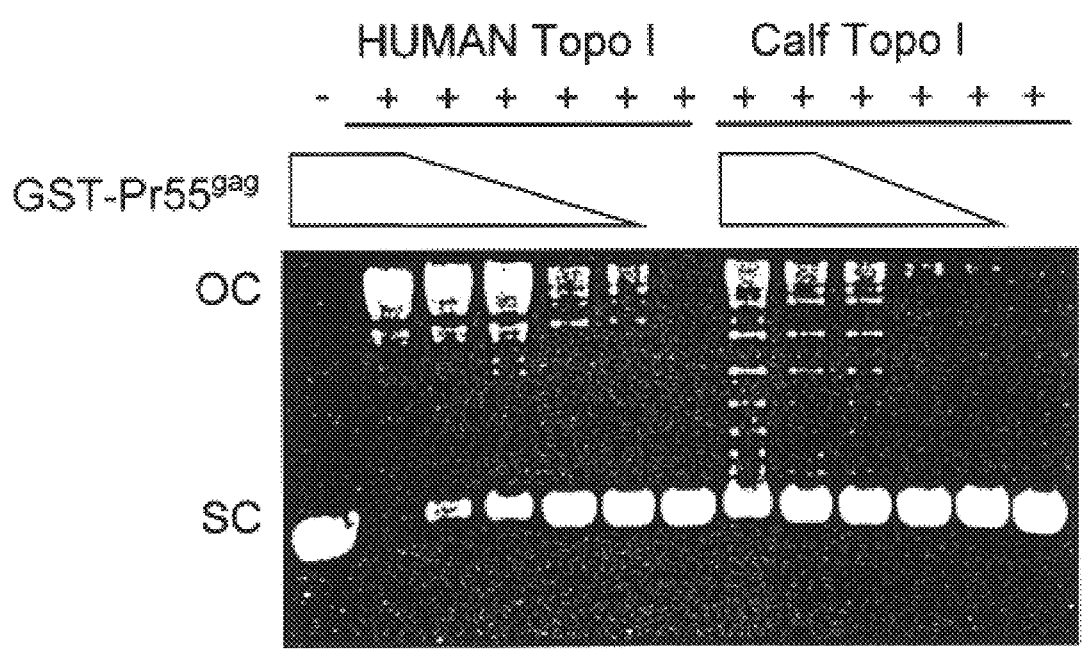
Figure 7A:
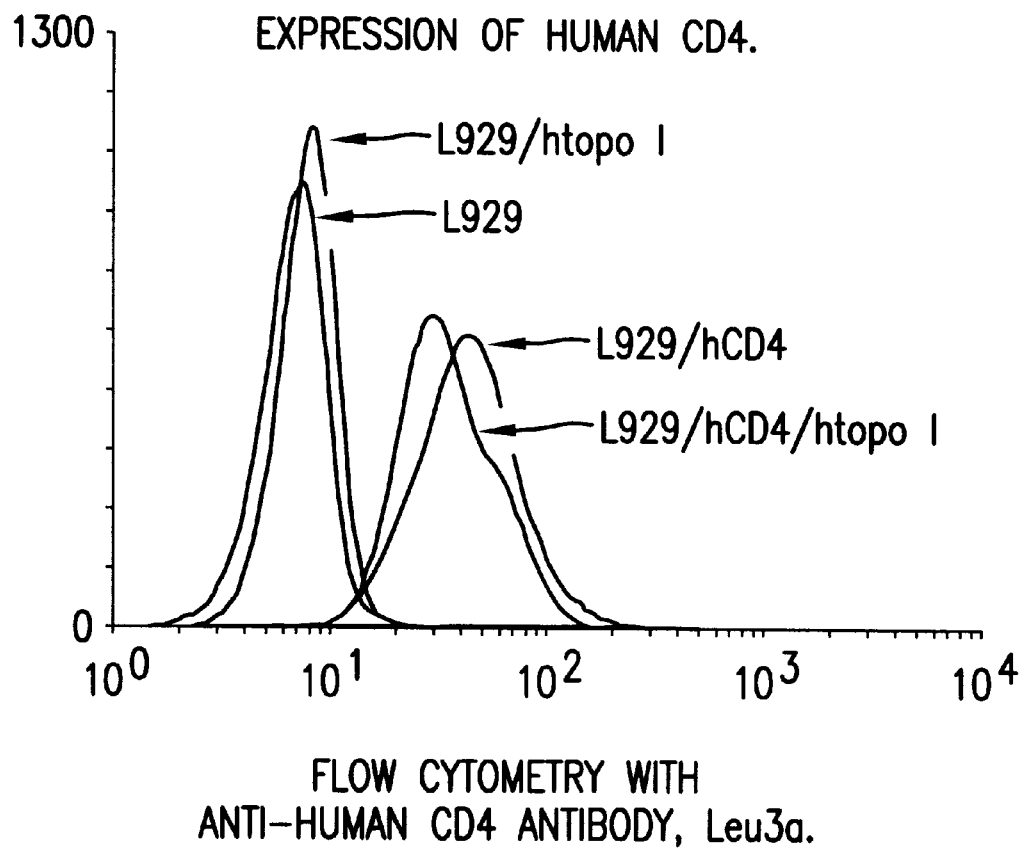
Figure 7B:
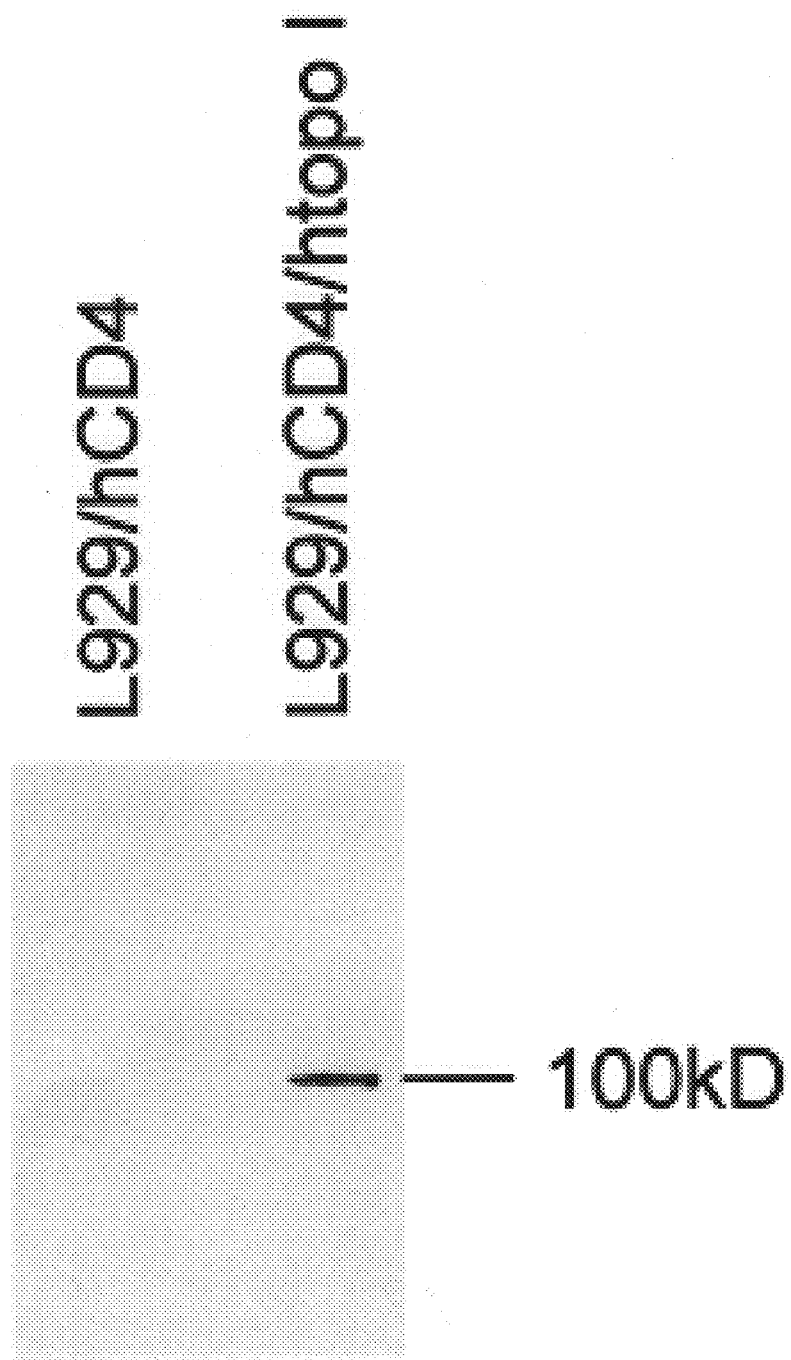

FIG. 6. Topo I activity after the interactions of human topo I or calf topo I with GST-Pr55gag. Five tenths microgram of supercoiled pUC19 DNA was incubated with 0.1 unit of human topo I or calf topo I and GST-Pr55gag at final concentrations of 50, 10, 2, 0.4, 0.08 µg/ml (+) for 15 minutes at 37° C. Reactions without topo I are indicated as FIG. 7. Establishment of murine cell lines stably expressing human CD4 and human topoisomerase I. FIG. 7A. Selected cell lines were stained with Leu3a and FITC conjugated goat anti-mouse sera and analyzed by flow cytometry as indicated. FIG. 7B. Expression of c-myc epitope tagging human topo I. The murine fibroblast cell line stably expressing CD4 was again stably transfected with control expression vector or c-myc epitope-tagging human topo I expression vector in the presence of Hygromycine resistant vector were analyzed by immunoblotting with rabbit anti-myc serum.

Figure 8A:
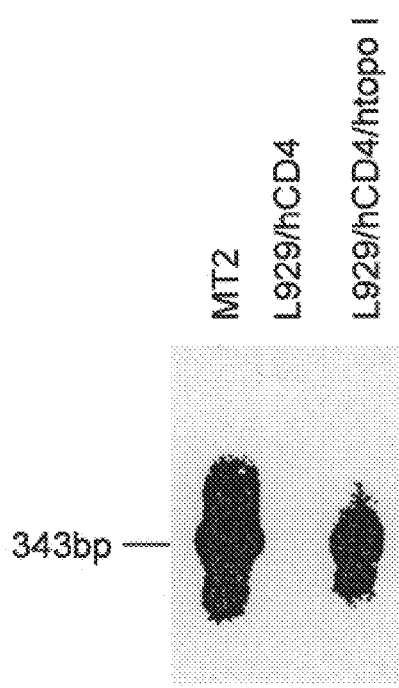
Figure 8B:
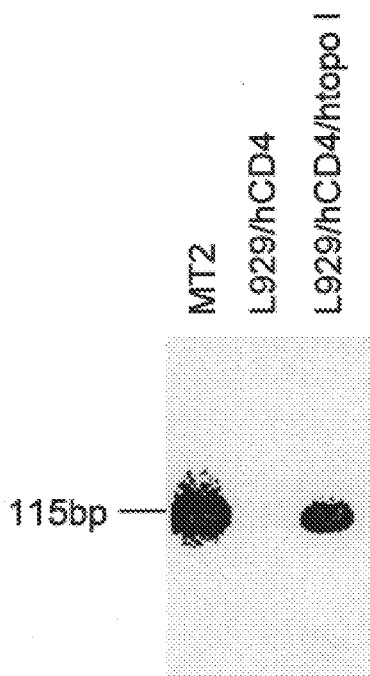

FIG. 8. Investigation of the role of human topo I on HIV-1 reverse transcription in L929 cells. L929 cells were infected with HIV-1 (IIIB) by incubation for 24 hrs. and following trypsinization, cells were incubated further 7 days. Proviral DNA synthesis was analyzed by polymerase chain reaction (PCR) techniques employing gag(c) or U3–U5 (d) specific primers. PCR using the primers for gag-amplification, SK38, 5'ATAATCCACCTATCCCAGTAGGAGAAAT3' (1544–1571) and SK39, 5'TTTGGTCCTTGTCTTATGTC-CAGAATGC3' (1631–1658) or U3–U5-amplification, HL30,5,GACAGCCTCCTAGCATTTCGTCAC3' (265–288) and HL10, 5'AGGGTCTGAGGGATCTCTAG3' (588–607). It can be seen that in the cells expressing only human CD4 (L929/hCD4) provirus could not be detected. In contrast, in the cells expressing both human CD4 and complete topo I (L929/hCD4/htopoI), provirus could be readily detected.

Figure 9:
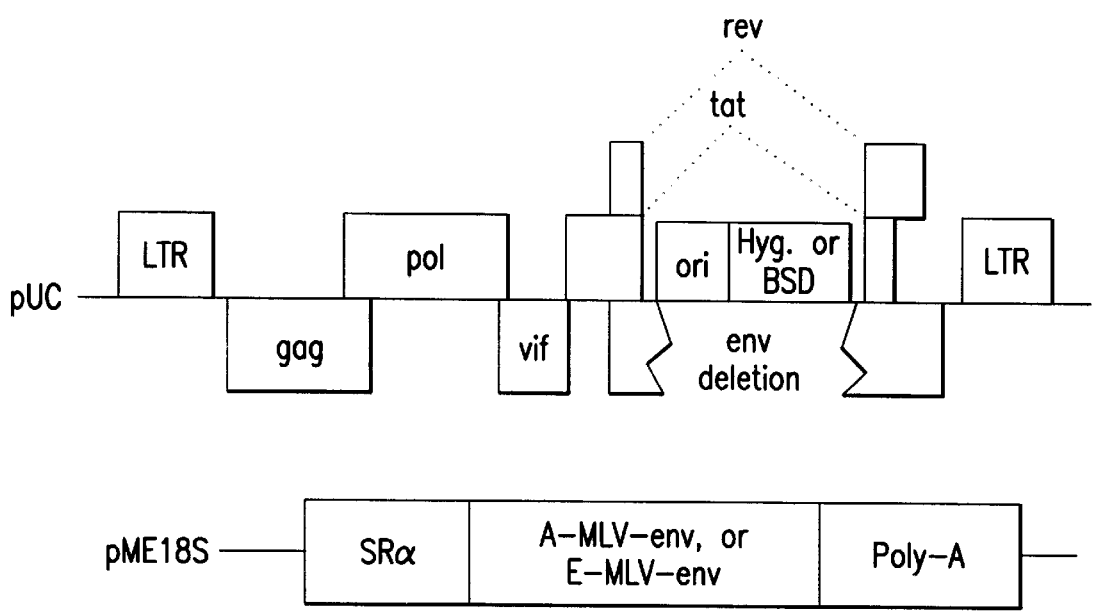

FIG. 9. Recombinant plasmids for the production of HIV-1 pseudotype. FIG. 9A. The recombinant HIV-1 vector. A 1.2 kb deletion in the env gene of pNL43 was made, leaving the rev responsive element and tat and rev exons intact. SV40 ori and hygromycine or brastcydine resistant sequences were inserted into the env deletion site. These constructs were named as HIV-hyg or HIV-BSD respectively. FIG. 9B. Structure of the MLV ecotropic env expression vector. Transcription is driven by $SR_\alpha$ promoter.

Figure 10:
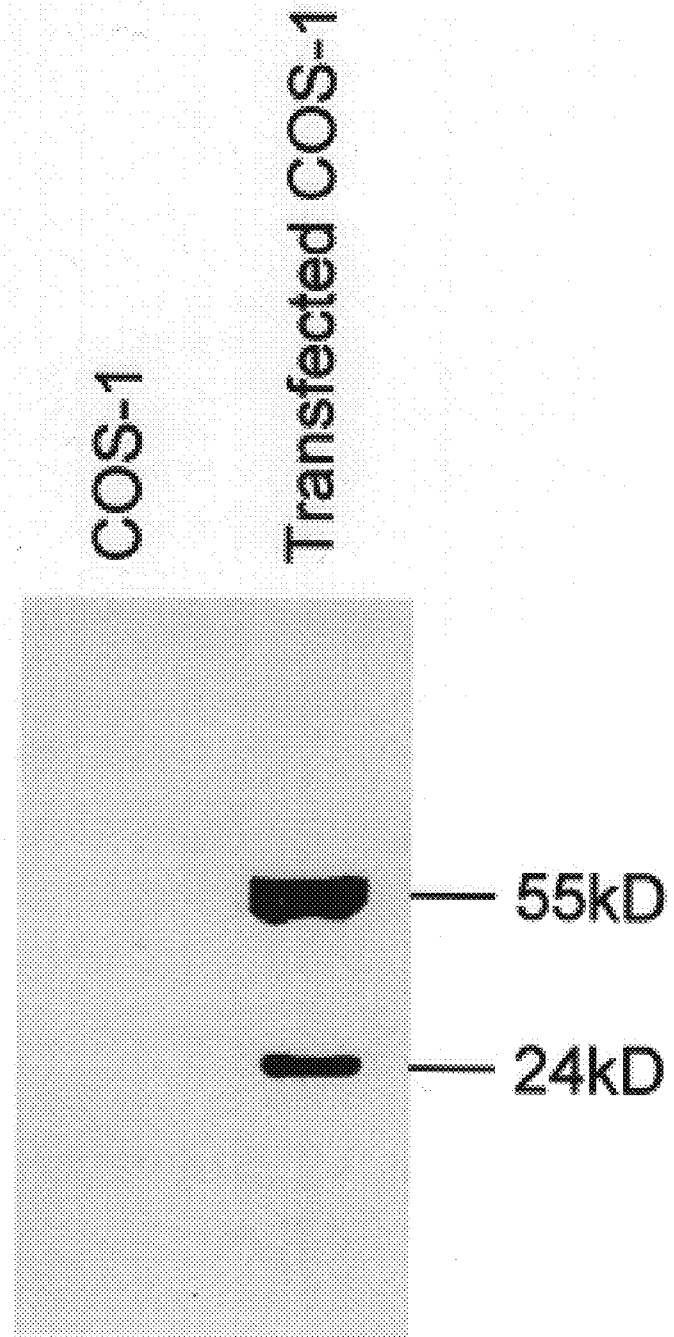

FIG. 10. Immunoblot analysis of gag proteins expressed by COS1 cells transfected with HIV-hyg. When HIV-hyg or HIV-bsd and MLV-eco were cotransfected into COS-1 cells, bands corresponding to the processed (p24) and precursor form (p55) of HIV-1 gag proteins were observed.

FIG. 11. Nucleotide sequence of human topoisomerase I Genebank Accession Number N83271.

Figure 12:
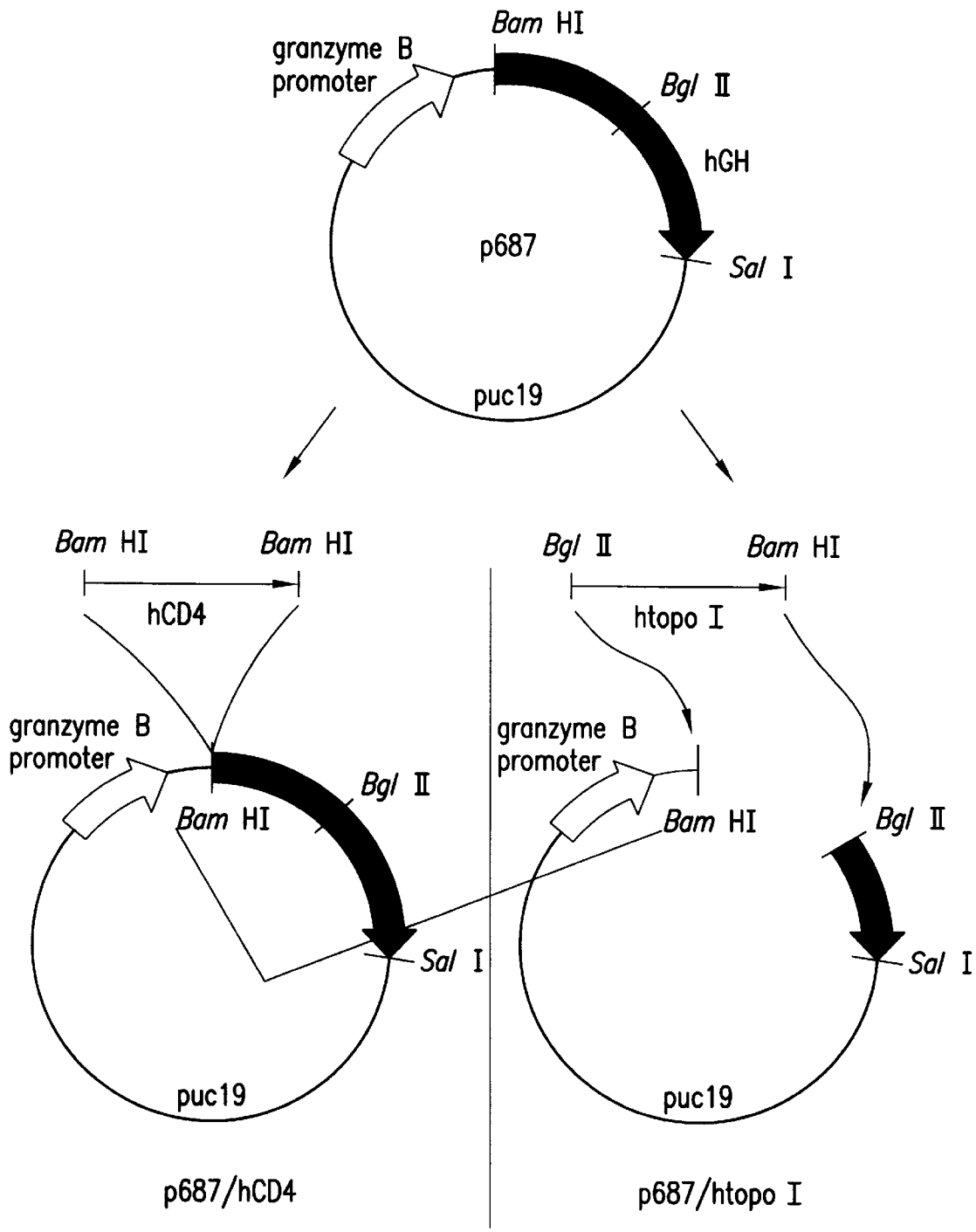

FIG. 12. Construction of plasmids expressing human CD4 or human topoisomerase I under the granzyme B promoter, which allows expression in peripheral blood cells and in particular NK cells and T lymphocytes. The p687 plasmid is derived from puc19. The hCD4 DNA was prepared by PCR amplification and inserted at the Bam Hl site of p687. The Bgl II/Bam HI fragment of the htopo I sequence (as described in FIG. 11) was inserted at the Bam HI/Bgl II site of p687. Both plasmids were linearized by digestion with SalI prior to microinjection.

Figure 13:
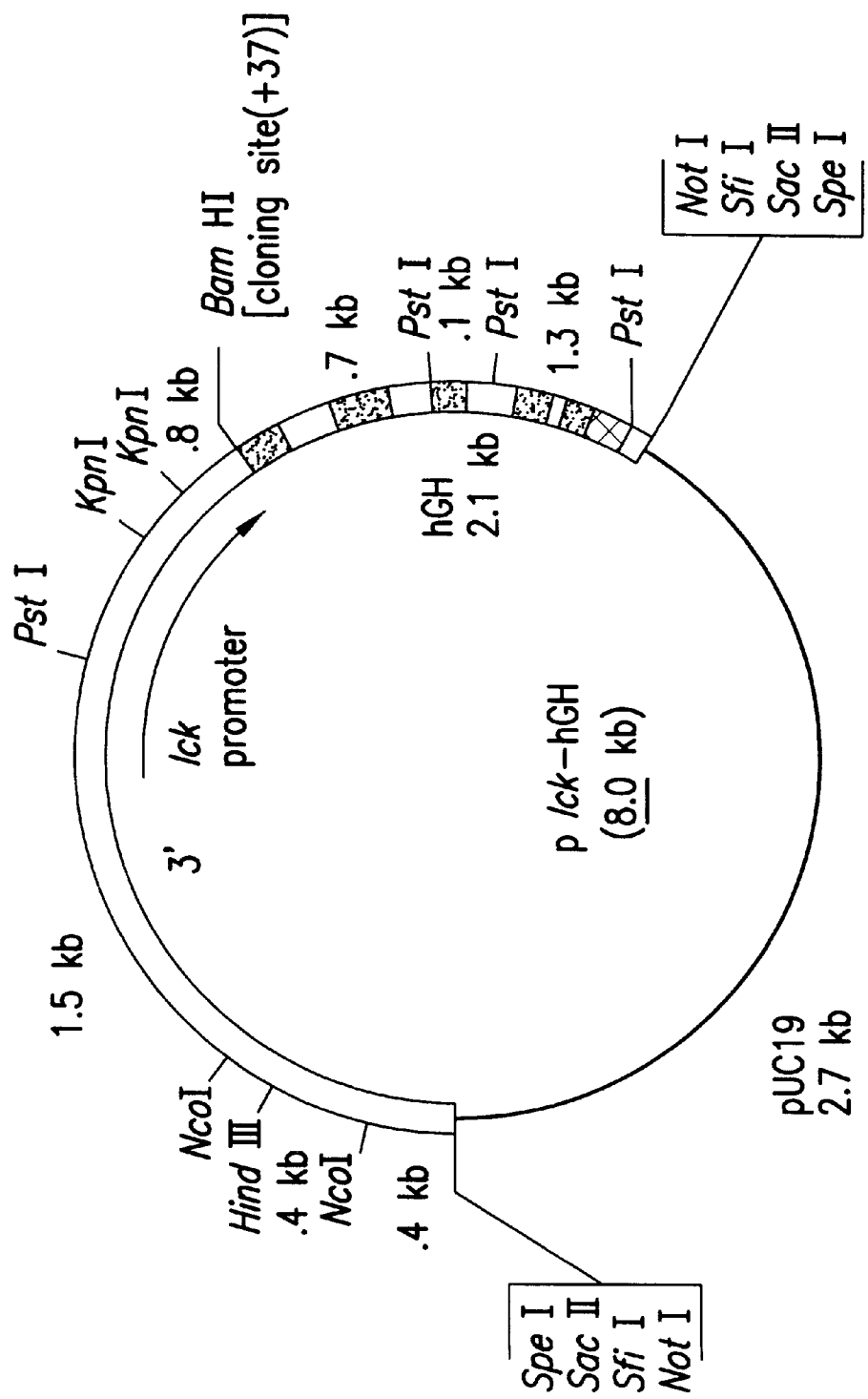

FIG. 13. Plasmid plck-hGH contains the lck promoter, which allows expression in peripheral T lymphocytes. The plasmid contains one Bam HI cloning site. The Bam HI/Bgl II fragment of the htopo I sequence (as described in FIG. 11) was inserted at the Bam HI site of plck-hGH. The hCD4 DNA was prepared by PCR amplification and inserted at the Bam HI site of plck-hGH.

5. DETAILED DESCRIPTION OF THE INVENTION

The present invention relates to therapeutic protocols and pharmaceutical compositions designed to target topo I for the treatment of HIV infection. The invention relates to therapeutic modalities and pharmaceutical compositions for the treatment of HIV-infection using human topo I and its interaction with HIV gag and RT as a target for intervention. The invention further relates to the use of human topo I to enhance the activity of RT.

The present invention relates to targeting human topo I and/or the interaction between human topo I and HIV proteins gag and RT as a means for treating HIV infection. The invention is based, in part, on the Applicants' discovery of the specific interaction between human topo I and HIV proteins gag and RT and the requirement of this interaction to support HIV replication.

The present invention relates to therapeutic modalities and pharmaceutical compositions for the treatment of HIV infection; these agents are designed to interfere with the interaction between human topo I and HIV proteins gag and RT. A variety of techniques and compositions may be utilized to inhibit the interaction of topo I and HIV proteins gag and RT, thereby inhibiting HIV-infection.

The invention further relates to a murine model for HIV replication, in which transgenic mice express human topo I alone or the CD-4 cell surface protein and human topo I. These transgenic mice are able to support HIV life cycle (i.e., entry, replication and assembly). The transgenic mice of the present invention have utility as a screen to identify other host cellular components required to support the HIV life cycle. In a preferred embodiment of the invention these transgenic mice have utility in screening T cell genomic libraries to identify additional human proteins required to support the HIV life cycle. These transgenic mice also have utility as a screen for drugs and compounds which may have anti-HIV activity.

Another embodiment of the invention relates to small organic molecules that interfere with the human topo I or the interaction of human topo I and HIV proteins to inhibit HIV infection. The present invention additionally relates to screening assays to identify compounds which inhibit HIV infection, these compounds are selected for their activity in inhibiting human topo I or blocking the interaction between human topo I and HIV proteins gag and RT. Such identified compounds would have utility in the treatment and prevention of HIV-infection.

The therapeutic modalities of the invention further encompass combination therapy in which an agent which interferes with the interaction of human topo I and HIV protein and at least one other therapeutic agent are administered either concomitantly, e.g., as an admixture, separately but simultaneously or concurrently; or sequentially, including cycling therapy. Cycling therapy involves the administration of a first antiviral compound for a period of time, followed by the administration of a second antiviral compound for a period of time and repeating this sequential administration, i.e., the cycle, in order to reduce the development of resistance to one of the therapies.

The novel antiviral combinations of the present invention provide a means of treatment which may not only reduce the effective dose of either drug required for antiviral activity, thereby reducing toxicity, but may also improve the absolute antiviral effect as a result of attacking the virus through multiple mechanisms. Similarly, the novel antiviral combinations provide a means for circumventing the development of viral resistance to a single therapy, thereby providing the clinician with a more efficacious treatment.

Therapeutic agents to be used in combination with a topoisomerase I inhibitor encompass a wide variety of known treatments. Preferably, the combinations employ a topo I inhibitor in combination with agents with a different mode of attack. Such agents include but are not limited to: antivirals, such as cytokines, inhibitors of reverse transcriptase, inhibitors of viral capping, and inhibitors of viral protease.

The present invention still further relates to the Applicants' discovery that the ability of topo I to enhance the activity of endogenous RT can be utilized to improve the efficiency of gene therapy.

5.1. The Role of Human Topo I and its Interaction with HIV GAG and RT in HIV Infection The present invention is based, in part, on the Applicants' surprising discovery that (1) human topo I interacts with and is activated by HIV gag in a species specific manner; (2) the interaction between human topo I and gag is required to enhance HIV RT activity: and (3) the interactions between human topo I and HIV gag and RT are required to support HIV replication. This model is based on the Applicant's observation that although murine cells expressing human CD4 are not capable of supporting HIV replication (Maddon et al., 1986, Cell 47: 333–348), murine cells expressing both human CD4 and human topo I are able to support HIV replication. This discovery is exemplified in Sections 6, 7 and 8 infra, which demonstrate that the activation of human topo I by gag is species specific, in that the enhancement of calf or mouse topo I activity could not be detected in the presence of HIV gag, even at high concentrations of gag. The expression of human topo I was shown to enhance the activity of HIV RT in murine cells.

That human topo I interacts with and is activated by HIV gag, and that this complex is required for activation of HIV RT is further supported by the working examples described infra which demonstrate (1) that gag proteins activate cellular topo I in a species specific manner; (2) mouse cells expressing human CD4 and topo I infected with HIV effectively reverse transcribe the HIV RNA genome; and (3) the topo I inhibitor, TAN134A, which attacks the topo I active site directly, inhibits RT activity in murine cells.

5.2. Human Topo I as a Target for Intervention in the Treatment of HIV Infection As discussed above, the Applicants' work shows that inhibition of human topo I or the interaction between human topo I and HIV proteins is effective in inhibiting cellular infection by HIV. A variety of techniques and compositions may be utilized to target human topo I to inhibit its activity or to inhibit the interaction between human topo I and HIV proteins, thereby inhibiting HIV infection.

For example, compounds which may be used in accordance with the present invention encompass any compound which targets human topo I to inhibit its activity or interferes with the interaction between human topo I and its activation by HIV gag or its ability to activate HIV RT, including but not limited to neutralizing antibodies against human topo I, or HIV proteins gag and RT. Other examples of compounds include but are not limited to peptides (such as, for example, peptides representing those regions of human topo I required for its interaction with HIV gag or RT), phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof). Techniques for determination of effective doses and administration of such compounds are described below, in Section 5.6 infra.

In addition, compounds which may also be used in accordance with the present invention, include intracellular drugs that inhibit human topo I activity—competing ligands that prevent HIV gag from interacting with human topo I—and competing ligands that prevent the HIV gag and topo I complex from interacting with HIV RT.

Gene therapy approaches may also be used in accordance with the present invention to inhibit the interaction of human topo I and HIV proteins. Among the compounds which may disrupt the interaction of topoisomerase with its viral targets gag and RT are antisense, ribozyme and triple helix molecules. Such molecules are designed to inhibit the expression of the target gene, topoisomerase I, in HIV-infected host cells. Techniques for the production and use of antisense ribozyme and/or triple helix molecules are well known to those of skill in the art and can be designed with respect to the cDNA (or mRNA) sequence of topo I as shown in FIG. 11.

Antisense RNA and DNA molecules act to directly block the translation of mRNA by hybridizing to targeted mRNA and preventing protein translation. With respect to antisense DNA, oligodeoxynucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA. (For a review see Rossi, J., 1994, Current Biology 4:469–471). The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence see U.S. Pat. No. 5,093,246, which is incorporated by reference in its entirety. As such within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridize with complementary oligonucleotides, using ribonuclease protection assays.

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may be introduced into cells via gene therapy methods such as those described, that do not contain sequences susceptible to whatever antisense, ribozyme, or triple helix treatments are being utilized. Alternatively, in instances whereby the target gene encodes an extracellular protein, it may be preferable to coadminister normal target gene protein in order to maintain the requisite level of target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters'such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.3. The Murine HIV Model System

The present invention relates to the expression of topo I and the co-expression of human CD4 and topo I in cell lines or in transgenic animals as a system which supports the HIV life cycle as a means of (1) identifying additional factors required to support the HIV life cycle and (2) as a system to screen test compounds, for their ability to interfere with the interaction between human topo I and HIV gag and RT. In a preferred embodiment of the invention, human topo I is expressed alone or human CD4 and topo I are co-expressed in mouse cell lines and transgenic mice.

In a further embodiment of the invention, human topo I is expressed in mouse cells or in transgenic mice. In this embodiment of the invention, internalization of the HIV virus by mouse cells is bypassed by a HIV pseudovirus. The HIV pseudovirus contains the HIV virus and an envelope protein from a virus with a natural tropism for mouse cells, such as the murine leukemia viruses (MLV). Therefore, the HIV virus is internalized by the mouse cells efficiently. These cells can then support the life cycle of the internalized HIV virus, because they express human topo I.

The present invention encompasses the expression of human topo I in animals and cells lines in order to support HIV replication. The present invention further encompasses the co-expression of human topo I and other human proteins, such as CD4, or the use of HIV pseudoviruses to promote internalization of the HIV virus.

5.3.1. Expression of Human CD4 and Human Topo I

The topo I and CD4 gene products or peptide fragments thereof, may be produced by recombinant DNA technology using techniques well known in the art. Thus, methods for preparing the topo I and CD4 gene polypeptides and peptides of the invention by expressing nucleic acid containing topo I and CD4 gene sequences are described herein. Methods which are well known to those skilled in the art can be used to construct expression vectors containing topo I and CD4 gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding topo I and CD4 gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the topo I and CD4 gene coding sequences of the invention. Such host-expression systems represent vehicles by which the coding sequences of interest may be produced and subsequently purified, but also represent cells which may, when transformed or transfected with the appropriate nucleotide coding sequences, exhibit the topo I and CD4 gene product of the invention in situ. These include but are not limited to microorganisms such as bacteria (e.g., E. coli, B. subtilis) transformed with recombinant bacteriophage DNA, plasmid DNA or cosmid DNA expression vectors containing topo I and CD4 gene product coding sequences; yeast (e.g., Saccharomyces, Pichia) transformed with recombinant yeast expression vectors containing the topo I and CD4 gene product coding sequences; insect cell systems infected with recombinant virus expression vectors (e.g., baculovirus) containing the topo I and CD4 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing topo I and CD4 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the topo I and CD4 gene product being expressed. For example, when a large quantity of such a protein is to be produced, for the generation of pharmaceutical compositions of topo I and CD4 protein or for raising antibodies to topo I and CD4 protein, for example, vectors which direct the expression of high levels of fusion protein products that are readily purified may be desirable. Such vectors include, but are not limited, to the E. coli expression vector pUR278 (Ruther et al., 1983, EMBO J. 2:1791), in which the topo I and CD4 gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The topo I and CD4 gene coding sequence may be cloned individually into non-essential regions (for example the polyhedrin gene) of the virus and placed under control of an AcNPV promoter (for example the polyhedrin promoter). Successful insertion of topo I and CD4 gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the topo I and CD4 gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing topo I and CD4 gene product in infected hosts. (E.g., See Logan & Shenk, 1984, Proc. Natl. Acad. Sci. USA 81:3655–3659). Specific initiation signals may also be required for efficient translation of inserted topo I and CD4 gene product coding sequences. These signals include the ATG initiation codon and adjacent sequences. In cases where an entire topo I and CD4 gene, including its own initiation codon and adjacent sequences, is inserted into the appropriate expression vector, no additional translational control signals may be needed. However, in cases where only a portion of the topo I and CD4 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

5.3.2. Expression of Human Topo I in Animal Cell Lines

The present invention encompasses the expression of human topo I and the co-expression of human CD4 and topo I in animal cell lines and their use as a system to support the HIV life cycle. In a preferred embodiment of the present invention, human CD4 and topo I are co-expressed in a mouse cell line. Host cell strain may be chosen which modulates the expression of the inserted sequences, or modifies and processes the gene product in the specific fashion desired. Such modifications (e.g., glycosylation) and processing (e.g. cleavage) of protein products may be important for the function of the protein. Different host cells have characteristic and specific mechanisms for the post-translational processing and modification of proteins and gene products. Appropriate cell lines or host systems can be chosen to ensure the correct modification of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38 cell lines.

For long term, high-yield production of recombinant proteins, stable expression is preferred. For example, cell lines which stably express the human CD4 and/or the human topo I gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines. This method may advantageously be used to engineer cell lines which express the human CD4 or human topo I gene products. Such cell lines would be particularly useful in screening and evaluation of compounds that affect the endogenous activity of the human topo I gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$·nitriloacetic acid-agarose columns and histidine-tagged proteins are selectively eluted with imidazole-containing buffers.

5.3.3. Expression of Human Topo I in Transgenic Animals

The present invention also encompasses the expression of human topo I and the co-expression of human CD4 and topo I in transgenic animals as a model system to support the HIV life cycle. In a preferred embodiment of the invention, human CD4 and human topo I are co-expressed in the same cells in transgenic mice. In another preferred embodiment of the invention, human topo I is expressed alone in transgenic mice and a HIV pseudovirus is used to infect the animals. For example, a HIV pseudovirus which contains the HIV virus and an envelope protein from a virus with a natural tropism for murine cells, such as the murine leukemia virus (MLV), is used to bypass internalization of the HIV virus by the murine cells. These murine cells can then support the life cycle of the internalized HIV virus, because they express human topo I.

The CD4 and topo I gene products can also be expressed together in transgenic animals. Animals of any species, including, but not limited to, mice, rats, rabbits, guinea pigs, pigs, micro-pigs, goats, and non-human primates, e.g., baboons, monkeys, and chimpanzees may be used to generate CD4 and topo I transgenic animals.

Any technique known in the art may be used to introduce the CD4 and topo I gene transgene into animals to produce the founder lines of transgenic animals. Such techniques include, but are not limited to pronuclear microinjection (Hoppe, P.C. and Wagner, T. E., 1989, U.S. Pat. No. 4,873, 191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the CD4 and topo I transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the CD4 and topo I gene transgene be integrated into the chromosomal site of the endogenous CD4 or topo I gene, gene targeting is preferred. Briefly, when such a technique is to be utilized, vectors containing some nucleotide sequences homologous to the endogenous topo I gene are designed for the purpose of integrating, via homologous recombination with chromosomal sequences, into and disrupting the function of the nucleotide sequence of the endogenous topo I gene. The transgene may also be selectively introduced into a particular cell type, thus inactivating the endogenous CD4 or topo I gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

In a preferred embodiment of the invention, human topo I and human CD4 are expressed in the same cells in the transgenic animals, in particular lymphocytes. For example, human CD4 and human topo I are expressed under the same cell type specific promoter, such as the granzyme B promoter which allows expression of topo I in peripheral blood cells and in particular NK cells and T lymphocytes (Wargnier et al., 1995, Mol. Cell. Biol. 92:6930–6934) or by expressing human topo I and human CD4 under a lck promoter (Allen et al. 1992, Mol. Cell. Biol. 12:2758–68; Wildin et al. 1995, J. Immunol. 155:1286–1295) which allows expression in peripheral CD4 T lymphocytes.

Once transgenic animals have been generated, the expression of the recombinant CD4 and topo I gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of CD4 or topo I gene-expressing tissue, may also be evaluated immunocytochemically using antibodies specific for the topo I transgene product.

5.4. The Use of Model Systems to Identify Additional Host Components Involved in the HIV Life Cycle The present invention further relates to the use of cell lines and transgenic animals expressing human topo I as a screen to identify other host cellular components required to support the HIV life cycle (viral entry, integration, replication and assembly). In particular, these transgenic mice have utility in screening T cell libraries to identify additional host components.

The present invention encompasses the identification of additional human T cell factors required to support the HIV life cycle, using the model animal systems decried herein. These additional T cell factors which are identified may also serve as targets for intervention in order to treat HIV-infection. The present invention also relates to therapeutic modalities and pharmaceutical compositions designed targeting any additional T cell factors as identified herein.

A genomic library can be constructed using DNA obtained from a human T cell line. Additionally, an expression library can be constructed utilizing cDNA synthesized from, for example, RNA isolated from human T cells. The human T cells may be derived from cell culture or from a patient. In this manner, gene products made by the T cells may be expressed in cell lines and/or transgenic animals to identify additional T cell components required to support the HIV life cycle.

In preparation of cDNA libraries, total RNA is isolated from human T cells. Poly(A)+ RNA is isolated from the total RNA, and cDNA prepared from the poly(A)+ RNA, all using standard procedures. See, for example, Sambrook et al., *Molecular Cloning: A Laboratory Manual*, 2d ed., Vol. 2 (1989). The cDNAs may be synthesized with a restriction enzyme site at their 3'-ends by using an appropriate primer and further have linkers or adaptors attached at their 5'-ends to facilitate the insertion of the cDNAs into suitable cDNA cloning vectors. Alternatively, adaptors or linkers may be attached to the cDNAs after the completion of cDNA synthesis.

In preparation of genomic libraries, DNA is isolated from human T cells and fragments are generated. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including but not limited to, agarose and polyacrylamide gel electrophoresis, column chromatography and sucrose gradient centrifugation.

The genomic DNA or cDNA fragments can be inserted into suitable vectors, including but not limited to, plasmids, cosmids, bacteriophages lambda or $T_4$, and yeast artificial chromosome (YAC) [See, for example, Sambrook et al., *Molecular Cloning: A Laboratory Manual*, 2d ed., Cold Spring Harbor Laboratory Press, Cold Spring Harbor, N.Y. (1989); Glover, D. M (ed.), *DNA Cloning: A Practical Approach*, MRL Press, Ltd., Oxford, U.K., Vols. I and II (1985)].

The DNA or RNA should be at least 17 nucleotides, preferably at least 26 nucleotides, and most preferably at least 50 nucleotides in length. The nucleotide probe is hybridized under moderate stringency conditions and washed under moderate, preferably high stringency conditions. Clones in libraries with insert DNA having substantial homology to the target probe will hybridize to the probe. Hybridization of the nucleotide probe to genomic or cDNA libraries is carried out using methods known in the art. One of ordinary skill in the art will know that the appropriate hybridization and wash conditions depend on the length and base composition of the probe and that such conditions may be determined using standard formulae. See, for example, Sambrook et al., *Molecular Cloning: A Laboratory Manual*, 2nd ed., Cold Spring Harbor Laboratory Press, Cold Spring Harbor, N.Y., Vol. 2, (1989) pp 11.45–11.57 and 15.55–15.57.

The identity of a cloned or amplified gene sequence can be verified by comparing the amino acid sequences of its three open reading frames with the amino acid sequence of known gene. The identity of the cloned or amplified gene sequence may be further verified by examining its expression pattern.

Comparison of the amino acid sequences encoded by a cloned or amplified sequence may reveal that it does not contain the entire gene or its promoter. In such a case the cloned or amplified gene sequence may be used as a probe to screen a genomic library for clones having inserts that overlap the cloned or amplified gene sequence. A complete gene and its promoter may be reconstructed by splicing the overlapping gene sequences.

The ability of an additional T cell factor to enhance the HIV life cycle may be assayed in a number of ways, including but not limited to, measuring the level of HIV specific transcripts, measuring HIV RT activity, or measuring the level of HIV provirus. These assays are well known to those skilled in the art and in addition have been described infra. The ability of the expression of the additional T cell factor to support the HIV life cycle will be compared to those systems in which only human CD4 and topo I are expressed.

5.5. The Use of the Model System to Screen for Anti-HIV Agents

The present invention further relates to the model systems as described in Sections 5.3 infra as assay systems to screen test compounds, such as drugs, ligands (natural or synthetic), proteins, peptides and small organic molecules for their ability to interfere with the interaction between human topo I and HIV gag and RT, and therefore have utility as an anti-HIV agent.

The following assays are designed to identify compounds or compositions that interfere with the interaction between topo I and HIV proteins gag and RT. Compounds may include, but are not limited to, small molecules, peptides such as, for example, soluble peptides, including but not limited to, small molecules, peptides such as, for example, soluble peptides, including but not limited to, peptides comprising portions of topo I or the regions of topo I required for its interaction with HIV gag or RT, antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules. The compounds identified as inhibitors of the interaction between topo I and HIV proteins.

The principle of the assays to identify compounds which inhibit the interaction of topo I and HIV proteins, in particular gag and RT involves administering the compound to mouse cells stably expressing both human CD4 and topo I or to transgenic mice expressing both human CD4 and topo I infected with an appropriate concentration (i.e., TCID$_{50}$) of HIV virus. Culture conditions well known to those in the art are used. A range of concentrations of the test compound may be used, in addition to a control culture wherein no test compound has been added. After incubation for an appropriate period (e.g., 7 days) of culturing, a cell-free supernatant is prepared, using standard procedures, and tested for the presence of RT activity as a measure of successful infection. The RT activity may be tested using standard techniques such as those described by, for example, Goff et al. (Goff et al., 1981, J. Virol. 38:239–248) and/or Willey et al. (Willey et al., 1988, J. Virol. 62:139–147). These references are incorporated herein by reference in their entirety.

The ability of the test compounds to inhibit HIV replication in mouse cells or transgenic mice may be assayed in a number of ways, including but not limited to, measuring the level of HIV specific transcripts, measuring HIV RT activity, measuring the level of HIV provirus or measuring the level of HIV virus. These assays are well known to those skilled in the art and in addition have been described infra. The ability of the test compound to inhibit the HIV life cycle will be compared to those systems in which only human CD4 and topo I are expressed.

5.6. Pharmaceutical Formulations and Methods of Administration

5.6.1. Antivirals to be Used in Combination with a Topoisomerase Inhibitor

According to the present invention, a topoisomerase I inhibitor, an inhibitor of HIV viral replication, may be used in combination with other therapeutic agents to enhance the antiviral effect achieved. Preferably a topoisomerase I inhibitor is used in combination with another antiviral agent. Such additional antiviral agents which may be used with a topoisomerase I inhibitor include but are not limited to those which function on a different target molecule involved in viral replication, e.g., reverse transcriptase inhibitors, viral protease inhibitors, glycosylation inhibitors; those which act on a different target molecule involved in viral transmission; those which act on a different loci of the same molecule; and those which prevent or reduce the occurrence of viral resistance. One skilled in the art would know of a wide variety of antiviral therapies which exhibit the above modes of activity.

A topoisomerase I inhibitor can also be used in combination with retrovirus inhibitors, such as nucleoside derivatives. Nucleoside derivatives are modified forms of purine and pyrimidine nucleosides which are the building blocks of RNA and DNA. Many of the nucleoside derivatives under study as potential anti-HIV medications result in premature termination of viral DNA replication before the entire genome has been transcribed. These derivatives lack 3' substituents that can bind to subsequent nucleosides and result in chain termination. Nucleoside derivatives such as 3'azido-3'-thymidine (AZT) and dideoxyinosine (ddI) have been exploited as inhibitors of HIV-1 replication, both in vitro and in vivo. Nucleoside analogs are the currently the only licensed therapeutics for the treatment of HIV infection and AIDS (Fischl et al, 1987 N. Engl. J. Med. 317, 185–191; Mitsuya and Broder, 1987 Nature 325, 773–778). This class of compounds works by inhibiting reverse transcriptase resulting in a block in cDNA synthesis (Mitsuya and Broder, 1987), these inhibitors work early in the infectious cycle of HIV-1 and inhibit integration into T-cell genome. However, AZT therapy leads to development of resistant HIV strains (Larder 1989, 1991, Ibid.) and demonstrates toxicity in AIDS patients upon long-term therapy (Fischl et al., 1987, N. Engl. J. Med. 317:185–191; Creagh-Kirk, et al., 1988, J.A.M.A. 260:3045–3048).

Further, a topoisomerase I inhibitor can be used in combination with nucleoside derivatives which include but are not limited to, 2',3'-dideoxyadenosine (ddA); 2',3-dideoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T) and 3'-azido-2',3'-dideoxythymidine (AZT). Alternatively, halogenated nucleoside derivatives may be used, preferably 2',3'-dideoxy-2'-fluoronucleosides including, but not limited to, 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; and 2',3'-dideoxy-2',3'-didehydro-2'-fluoronucleosides including, but not limited to 2',3'-dideoxy-2',3'-didehydro-2'-fluorothymidine (Fd4T). Preferably, the 2',3'-dideoxy-2'-fluoronucleosides of the invention are those in which the fluorine linkage is in the beta configuration, including, but not limited to, 2'3'-dideoxy-2'-beta-fluoroadenosine (F-ddA), 2',3'-dideoxy-2'-beta-fluoroinosine (F-ddI), and 2',3'-dideoxy-2'-beta-fluorocytosine (F-ddC). Such combinations allow one to use a lower dose of the nucleoside derivative thus reducing the toxicity associated with that agent, without loss of antiviral activity because of the use of the topoisomerase I inhibitor. Moreover, such a combination reduces or avoids viral resistance.

Preferred combinations of topoisomerase I inhibitors and nucleoside derivatives within the scope of the present invention include an effective amount of a topoisomerase I inhibitor and an effective amount of AZT to treat HIV infection; and an effective amount of a topoisomerase I inhibitor and an effective amount of ddI.

According to the present invention, topoisomerase I inhibitors can also be used in combination with uridine phosphorylase inhibitors, including but not limited to acyclouridine compounds, including benzylacyclouridine (BAU); benzyloxybenzylacyclouridine (BBAU); aminomethyl-benzylacyclouridine (AMBAU); aminomethyl-benzyloxybenzylacyclouridine (AMB-BAU);

hydroxymethyl-benzylacyclouridine (HMBAU); and hydroxymethyl-benzyloxybenzylacyclouridine (HMBBAU).

According to the present invention, topoisomerase I inhibitors can be used in combination with viral protease inhibitors, including but not limited to, Invirase (saquinavir, Roche), ABT-538 (Abbott, CAS Reg. No. 155213-67-5), AG1343 (Burroughs Wellcome/Glaxo, CAS Reg. No. 161814-49-9). Protease inhibitors are generally thought to work primarily during or after assembly (i.e., viral budding) to inhibit maturation of virions to a mature infectious state. For example, ABT-538 has been shown to have potent antiviral activity in vitro and favorable pharmokinetic and safety profiles in vivo (Ho, et al., 1995, Nature 373: 123–126). Administration of ABT-538 to AIDS patients causes plasma HIV-1 levels to decrease exponentially and CD4 lymphocyte counts to rise substantially. The exponential decline in plasma viraemia following ABT-538 treatment reflects both the clearance of free virions and the loss of HIV-1 producing cells as the drug substantially blocks new rounds of infection. ABT-538 treatment reduces virus-mediated destruction of CD4 lymphocytes. Combining this treatment with topoisomerase I inhibitors, which inhibits at an earlier stage of HIV infection, viral fusion, would be likely to have synergistic effects and have a dramatic clinical impact.

In order to evaluate potential therapeutic efficacy of topoisomerase I inhibitors in combination with the antiviral therapeutics described above, these combinations may be tested for antiviral activity according to methods known in the art.

A compound of the invention can be administered to a human patient by itself or in pharmaceutical compositions where it is mixed with suitable carriers or excipients at doses to treat or ameliorate various conditions involving HIV-infection. A therapeutically effective dose further refers to that amount of the compound sufficient to inhibit HIV infection. Therapeutically effective doses may be administered alone or as adjunctive therapy in combination with other treatments for HIV infection or associated diseases. Techniques for the formulation and administration of the compounds of the instant application may be found in "Remington's Pharmaceutical Sciences" Mack Publishing Co., Easton, Pa., latest addition.

5.6.2. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer the agent of the present invention in a targeted drug delivery system, for example in a liposome coated with an anti-CD4 antibody. The liposomes will be targeted to and taken up selectively by cells expressing CD4.

5.6.3. Composition/Formulation

The pharmaceutical compositions of the present invention may be manufactured in a manner that is itself known, e.g., by means of conventional mixing, dissolving, dragee-making, levitating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are usually known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of the interaction between topoisomerase I and the viral proteins RT and gag may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate, malate sales, and the like.

5.6.4. Effective Dosage

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. Such information can be used to more accurately determine useful doses in humans.

A therapeutically effective dose refers to that amount of the compound that results in a reduction in the intensity of the infection or in amelioration of symptoms or a prolongation of survival in a patient. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–90% inhibition of HIV infection using the assays described herein. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In immunization procedures, the amount of immunogen to be used and the immunization schedule will be determined by a physician skilled in the art and will be administered by reference to the immune response and antibody titers of the subject.

5.6.5. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6. EXAMPLE

GAG Proteins Activate Cellular Topo I in a Species Specific Manner

The following in vitro experiments demonstrate that the HIV gag protein associates with human topo I in a species specific manner.

6.1. Materials and Methods

Cell lines and plasmids.

HeLa cells were grown in RPMI media containing 10% fetal calf serum.

The plasmid pHXB2, which contains the entire HIV-1 provirus was used as the source of HIV viral DNA (Ratner et al., 1985, Nature 313:277–284). A 5.1-kb SacI-SalI fragment of this plasmid encoding the gag, pol, and vif genes was employed for construction of the recombinant vaccinia viruses, expression vectors, and for oligonucleotide-directed mutagenesis.

Recombinant vaccinia viruses (RVVs) expressing the entire gag polyprotein Pr55gag, capsid protein p15, and the nucleocapsid protein p24 were prepared. For Pr55gag, primer Gag-C, 5'-TTAGTTGCCCCC AAGCTTTATTGTGACGAGGG-3' (nucleotides 1537–1669), was used to introduce a HindIII site followed by a stop codon (both underlined) using oligo-nucleotide-directed mutagenesis. After digestion with NcoI and HindIII, the fragment encoding Pr55gag was ligated to the same sites in the transfer plasmid vector pAK10. This plasmid pAK-Gag was used to generate RVVs using standard methods known in the art (Yasuda et al., 1990, J. Virol. 64:2788–2795; Hoshikawa et al., 1991, J. Gen. Virol. 72–2509)

Infection by RVVs and Immunoprecipitation of virus Proteins.

RVVs expressing the gag proteins and wild-type vaccinia virus were used to infect HeLa cells. At 16 hr postinfection, cells were lysed in phosphate-buffered saline containing 1% Nonidet P-40, and lysates were incubated with 5 µl of specific antibody to either p24 or P15 for 1 hr at 4 C. and subsequently with 50 µl of Sepharose-protein G for 1 hr at 4° C. For Pr55 gag and p24, a mouse monoclonal antibody directed against p24 (NU24) was used, and for p15 a sheep polyclonal antibody directed against the carboxyl terminus of P15 was used (Weiss et al., 1992, Gene 121:203–212). Precipitates were collected by centrifugation, washed three times with phosphate buffered saline containing 1% Nonidet P-40, and washed twice with 50 mM Tris-HCl (pH 8.0) containing 100 mM KCl/10 mM $MgCl_2$.

Assay of topo I Activity In Vitro.

Relaxation assays were carried out using purified GST-Pr55gag and GST proteins and with immunoprecipitations from RVV-infected cells. GST-Pr55gag and GST were used at final concentrations of 50, 10, 2, 0.4, and 0.008 µg/ml. Reaction mixtures containing 500 ng of supercoiled pUC19 DNA and human topo I at a final concentration of 0.1 unit per 20 µl of Tris HCl (pH 8.0), 100 mM KCl, 10 mM $MgCl_2$, 5 mM EDTA, and bovine serum albumin at 0.2 mg/ml. Reaction mixtures were allowed to proceed at 37° C. for 15 minutes and were terminated by the addition of 5 µl of Stop Solution [1% SDS/15% (vol/vol) glycerol/0.5 bromophenol blue]. Products were analyzed by agarose gel electrophoresis and staining with ethidium bromide.

6.2. Results

To determine if gag proteins were involved in topo I activity, HeLa cells were infected with a RVV expressing Pr55gag, and transfected with supercoiled DNA and then analyzed by Southern hybridization methods. Almost all of the transfected supercoiled DNA could be found in a relaxed form when Pr55gag was present (FIG. 1). The DNA remained predominantly in the supercoiled form when Pr55gag was absent. To determine if the Pr55gag had topo I activity or if this could be interacting with, and perhaps enhancing, cellular topo I activity, an in vitro relaxation assay was employed to determine if a GST-Pr55gag fusion protein had topo I activity. It could be demonstrated that GST-Pr55gag clearly enhanced cellular topo I activity (FIG. 2). No enhancement of topo I activity was noted with GST alone.

In order to identify the HIV-1 gag proteins involved in activation of topo I, HeLa cells were infected with RVVs expressing Pr55gag, p24, and P15 proteins. Protein complexes were immunoprecipitated with specific gag antibodies, and the topo I activity present in the precipitates was analyzed. Relaxation activity was associated with only the Pr55gag and the P15 proteins, suggesting that the latter was responsible for the activation of topo I. No activity was noted in precipitates or p24 or wild-type vaccinia virus.

These results clearly show that the nucleocapsid protein P15 could activate and enhance cellular topo I activity and that the topo I activity associated with HIV-1 is of cellular origin.

7. EXAMPLE

HIV RT ACTIVITY is Enhanced by Interaction with Cellular Topo I

The following in vitro experiments demonstrate that the HIV RT activity is enhanced by interacting with human topo I in a species specific manner.

7.1. Materials and Methods

RNA Templates.

Three templates were prepared. A template containing representative 5' and 3' ends of HIV RNA was prepared from plasmid pAD which was constructed as follows. PCR was used to prepare two products (AB and CD) from plasmid pHXB2 (Ratner et al., 1985, Nature 313:277–284). For AB, primers employed were A, 5'-CTGCATATAG AATTCTAATACGACTCATAGGGTCTCTC-3' (nucleotides 422–462), and B, 5'GCACTGGATCTACTCTA-3' (nucleotides 1424–1441). The former contains an EcoRI site following by the T7 polymerase promoter (both underlined). For CD, primers employed were C, 5'CATTCGATTAGTGAACGG-3' (nucleotides 8489–8506), and D, 5'-AGATACCAG TCTAGA(TTT)$_8$T-GAAGCACTCAAGGC-3' (nucleotides 9652–9666). Primer D contains an Xba I site (underlined) ad a poly(A) region (TTT)$_8$. Thirty cycles of denaturation for 30 sec at 94° C., primer annealing for 1 min at 52° C., and chain elongation for 1 min at 72° C. were performed. Product AB was digested with EcoRI, and CD was digested with BamHI and Xba I. After digestion, AB was ligated to pUC19 that had been digested with EcoRI and Sma I. After ligation the free end of the AB product was blunt-ended with the Klenow fragment of DNA polymerase I and then ligated to the Sma I site (plasmid pAB). Product CD was directly ligated to pUC19 that had been digested with BamHI and Xba I (plasmid pCD). Plasmid pAB was digested with Pst I, blunt-ended with the Klenow fragment, and then digested with Xba I. Plasmid CD was digested with BamHI, blunt-ended with the Klenow fragment, and then digested with Xba I. The insert resulting from the latter was directly ligated to treated pAB to produce plasmit pAD. RNA templates were produced after incubation with T7 polymerase (Ambion, Austin, Tex.) for 90 min at 37° C. with Xba I-linearized pAD. After digestion with DNase I, RNA was purified by phenol/chloroform extraction and ethanol precipitation. RNA templates containing only the 3' or 5' regions of HIV RNA were prepared from two plasmids pAD 3' and pAD 5', which were constructed as follows. To construct pAD 3' and pAD 5', which were constructed as follows. To construct pAD 3', pAD was digested with Xho I and Xba I, and the insert was directly ligated to pBluescript SKII (Stratagene). To construct pAD 5', pAD was digested with Acc I and Xba I; after Klenow treatment, the vector and insert were directly religated. RNA templates were prepared from plasmids linearized by Xba I and Xmn I digestion, respectively, and purified as above.

Reverse Transcriptase (RT) Assays.

To analyze the influence of topo I on linear cDNA synthesis, the template containing both the 5' and 3' ends of HIV-1 RNA was used. cDNA synthesis expected to result in a product of 1481 nucleotides was initiated using a nef gene primer end-labeled with [$\theta$-$^{32}$P]ATP (5'-ACCCACCTCCTCCTCCTCTTGTGC-3'; nucleotides 9002–9027). Reaction mixtures obtained 300 ng of RNA template in 50 µl of 50 Mm TrisHCL (pH 8.0) containing 150 Mm KCl, 5 Mm MgCl$^2$, 5 Mm dithiothreitol, 0.5 Mm EGTA, 0.4 unit of RNasin (Promega), 0.1 unit of HIV-1 RT (Seikagaku, Kogyo, Tokyo), 100 ng of primer, 250 µM dNTPs, bovine serum albumin at 0.1 mg/ml, GST-P15 at 0.8 µg/ml 10 µl of glutathione beads (50% vol/vol; Pharmacia), and topo I at final concentrations of 0.16, 0.032 and 0.0064 unit. Samples were incubated at 37° C. for 25 min. To assay the inhibitory effects of camptothecin (CPT), reactions with topo I at a final concentration of 0.16 unit in the presence of 400, 40, 4 and 0 µM CPT were carried out. All reactions were terminated by the addition of 25 µl of stop solution [2% SDS/30% (vol/vol) formamide/0.1 % bromophenol blue/8% Ficoll] and incubation at 85° C. for 4 min. Samples were chilled on ice and electrophoresed on 1.2% agarose gels. Gels were dried onto nylon membranes and analyzed with a Fuji BAS2000 phosphorescence imager. To analyze the effect of topo I on the synthesis and transfer of strong stop DNA (ssDNA), the two RNA templates containing the 3' and 5' ends of HIV-1 RNA were used in equal concentrations (300 ng). cDNA synthesis was initiated using a primer corresponding to the primer binding site (PBS) (5'GTCCCTGTTCGGGCGCCA-3'; nucleotides 636–653) end-labeled with [$\theta$-$^{32}$p]ATP. Reaction conditions were as described above employing topo I at a final concentration of 0.16 unit/50-µl reaction volume. The final cDNA product would be expected to be 867 nucleotides in length. Inhibition of cDNA synthesis by CPT was carried out using final concentrations of 400, 40, and 4 µM. Reaction products were analyzed as above.

7.2. Results

These in vitro studies indicate that human topo I has a role in the activation of reverse transcription of HIV-1 RNA. To investigate the role of topo I in the reverse transcription of virus RNA, the effect of topo I on both linear and elongation of newly synthesized DNA on one strand, and synthesis and strand transfer of the ssDNA. A primer corresponding to the nef region was employed to initiate cDNA synthesis, which would be expected to produce a cDNA of 1481 nucleotides (FIG. 3A). cDNA synthesis was markedly enhanced by the presence of topo I, and this effect was clearly dependent on the concentration of the enzyme. cDNA synthesis could be inhibited by CPT, a specific topo I inhibitor, also in a concentration dependent manner.

By employing a primer corresponding to the primer binding site on one RNA template to permit synthesis of the ssDNA and a second to accommodate strand transfer, cDNA synthesis was monitored. It can be seen that a cDNA product of 867 nucleotides, which consists of the 200-nucleotide ssDNA and the 667-nucleotide fragment produced after strand transfer, was synthesized in the presence of topo I (FIG. 4A). It can be seen that this could be inhibited by CPT in a concentration-dependent manner (FIG. 4B). The radio-activity evident in the lower part of the gel represents both strong stop and intermediate size cDNA products. It can be seen that the greatest levels of these are produced in reactions containing the highest concentrations of CPT, suggesting that the drug is inhibiting chain elongation rather than the strand transfer step.

8. EXAMPLE

Mouse Cells Expressing Human CD4 and Topo I Effectively Support HIV Infection Human CD4 expressing mouse cells are not a natural substrate for infection with HIV. In order to show that species specificity accounts for the poor reverse transcription of the HIV genome in HIV-infected mouse cells, HIV infection was attempted in mouse cells expressing both human CD4 and topoisomerase.

8.1. Materials and Methods

The fragment of EcoRI and BamHI of human CD4 cDNA was subcloned into mammalian expression vector, pEFBOS (Mizushima et al., 1990, Nuc.Aci. Res. 18:5322). Murine cell line, L929 were transfected with human CD4 expressing vector by phosphate method. After 48 hrs, G418 (BRL) was added to 400 µg/ml. Fifteen days after selection, several colonies were examined for CD4 expression with anti-CD4 monoclonal antibody, Leu3a (Becton Dickinson). Selected colonies were again cloned and used as CD4 positive L929. This cell line were stained with Leu3a and FITC conjugated goat anti-mouse sera (Becton Dickinson) at 1:50, in the presence of 2% fatal calf serum. Relative fluorescence intensity was detected by flow cytometry.

For tagging human topo I with c-myc epitope, the sequence MEQKLISEEDL was inserted at the N-terminus of human topo I. To accomplish this the double stranded oligonucleotide 5'-GAA TTC GCC ATT ATG GAG CAG AAG CTG ATC TTC GAG GAG GAC CTG GCC ATG G GCT AGC-3' was ligated into the Sma I site of pUC19. (underlines indicate EcoRI, NcoI and Nhe I respectively) PCR was used to prepare human topo I cDNA carrying Nco I and Xba I site at its 5' and 3' site respectively, with two primers, 5'-CGT CCC TCC CCA TGG ACA TGA GTG GGG A-3' and 5'-GCC TCT TGA TCT AGA AAA CTC ATA-3' (underlines indicated Nco I and Xba I respectively). PCR products was digested with Nco I and Xba 1. After digestion product was ligated to pUC-myc that had been digested with Nco I and Nhe 1. After ligation, the product was digested with Eco RI and again ligated to expression vector PXMN carrying chicken actin promoter, this final expression vector was designated as pMyc-topo I. C-myc epitope tagging human topo I carries the peptide, μMD between c-myc epitope and N-terminus of human topo I. To CD4 positive L929 cells, additionally myc-human topo I expression vector, pMyc-topo I was cotransfected with hygromycine resistant vector. Transfected cells were selected with hygromicine at 300 μg/ml and G418 at 400 μg/ml. Colonies were examined with anti-myc polyclonal serum.

L929 cells were infected with HIV-1 (IIIB) by incubation for 24 hrs. and following trypsinization, cells were incubated further 7 days. Proviral DNA synthesis was analyzed by PCR employing gag(c) or U3-U5(d) specific primers. PCR using the primers for gag-amplification, SK38, 5'ATAATC-CACCTATCCCAGTAGGAGAAAT3' (1544–1571) and SK39, 5'TTTGGTCCTTGTCTTATGTCCAGAATGC3' (1631–1658) or U3–U5-amplification, HL30, 5'GACAGCCTCCTAGCATTTCGTCAC3' (265–288) and HL10, 5'AGGGTCTGAGGGATCTCTAG3' (588–607) with 0.5 unit of *Thermus aquatics* DNA polymerize; 33 cycles of amplification were done consisting of 94 C. for 30 sec., 54° C. for 30 sec. and 72° C. for 30 sec. beginning with 2 min. at 94° C. and ending with 7 min. at 72° C. Buffer conditions included pH 8, 0, $Mg^{2+}$ 1.3 Mm. Reaction mixture was separated by electrophoresis on 2% agarose gel and subjected to Southern hybridization. Molecular mass marker was used to determined the size of the amplified DNA. PCR products at the same region were randomly labeled with ($\alpha$-$^{32}$P)dCTP and hybridized in Quickhybri solution (Strategen) as recommended by manufacturer.

8.2. Results

At first human CD4 was expressed in the mouse fibroblast L929 cell line. G418-selected transfectant clones were tested for their ability to bind mouse monoclonal antibody Leu3a which recognizes the gp120 binding region of the human CD4 molecule. The representative flow cytometry analyses demonstrates that expression of human CD4 on the mouse L929 cells. (FIG. 7A) Second, human topoisomerase I tagged with a c-myc epitope was expressed in the human CD4 expressing L929 cells. (FIG. 7B) Since human topo I and mouse topo I have 96% homology in amino acid sequence and 90% homology in cDNA sequence, it is impossible to distinguish them with an anti-human topo I antibody, therefore, the expression of human topo I in mouse cells was determined by Southern blot analysis with an anti-c-myc epitope sera.

To investigate the effect of human topo I on reverse transcriptase activity of the internalized HIV-1 genome, the mouse cells were infected for 24 hours with HIV-1. Total DNA was isolated and analyzed by PCR analysis with gag primers which should only be detected after reverse transcription of the HIV-1 genome has occurred in the infected cells. At day 7, no provirus was detected in cells expressing human CD4 alone, however in the cells expressing both human CD4 and topo I, provirus was well amplified. Cell lysates were also analyzed by PCR with the LTR(U3-U5) primers. (FIG. 8) Therefore, these results demonstrate that the expression of human topoisomerase I with human CD4 in mouse cells supports replication of HIV.

9. EXAMPLE

Mouse Cells Expressing Human Topo I Effectively Support HIV Infection

The following experiments demonstrate that once the HIV virus is internalized by mouse cells expressing human topo I, the human topo I is sufficient to support HIV replication. Internalization of the HIV virus by mouse cells expressing human topo I is bypassed by a HIV pseudovirus. The HIV pseudovirus contains the HIV core virus and an envelope protein with a natural tropism for mouse cells, such as the murine leukemia viruses (MLV). The HIV-1 pseudovirus contains murine leukemia virus env glycoproteins and a drug resistant gene, to bypass the poor internalization of RNA genome by mouse cells. After infection of pseudovirus effective reverse transcription and integration of the HIV genome is expected.

9.1. Materials and Methods

Construction of HIV-hyg, HIV-bsd and pSR-E-MLV-env plasmids. The pseudovirus was produced by cotransfection of HIV-hyg or HIV-bsd with the plasmid SRE-MLV-env that expresses the envelope glycoprotein of MLV. A 1.2 Kb deletion in the env gene of pNL43 the HIV-I vector was made, leaving the rev responsive element and tat and rev exons intact. (FIG. 9A and FIG. 9B) SV40 ori and hygromycine or brastcydine resistant sequences were inserted into the env deletion site. These constructs were named as HIV-hyg or HIV-BSD respectively. The HIV-BSD was constructed as follows: a 1.2 kb deletion in the envelope gene was made from Nde I (6399) to the Bgl II site (7611). Inserted at this site was a 0.35 kb fragment including the simian virus 40 origin of replication, and a 0.8kb fragment from pBSD from Bam HI to Pst I including promoter and coding sequence for the BSD, drug resistant gene. The HIV-Hyg. was constructed as follows: the hygromycine resistant sequences were obtained from plasmid pREP4 (Invitrogen) by PCR with primers, 5'-GTC GGC CGC TCT AGA CTG CTT CAT-3' and 5'-CCT CCC CCA TCT AGA CTA TTC CTT-3'. The underlined sequence indicates Xba I site. The PCR product replaced the brastcydine resistant sequences of HIV-BSD.

The SR-E-MLV plasmid contains the MLV ecotropic env coding sequences (Donis-Keller et al., 1980, Proc. Natl. Acad. Sci. 77:1642–1645) which were subcloned into the plasmid P18MES (FIG. 9).

Methods

Pseudovirus was generated by transfection of plasmid DNA into COS-1 cells by DEAE methods. 500 ng of each plasmid per 10 cm (diameter) dish of COS-1 cells was used, and 5 μM chloroquine was added to enhance transfection efficiency. At 4 hours after transfection, the medium was replaced with Dulbecco's modified Eagle medium containing 10% fetal calf serum and antibiotics. COS-1 culture supernatants were harvested from 48 to 64 hours after transfection, filtered through a 0.22 μm membrane, and without storage infected to L929 cells. L929 cells to be infected with pseudovirus were seeded into 6-well culture plates such that they were 60% confluent at the time of infection. Without dilution the supernatant including pseudovirus was added to the wells. Virus was allowed to absorb for 12 hrs. At 24 hrs later, cells were trypsinized and one fifth of cells per a well were spread to 10 cm dish. 2 days after hygromycine or brastcydine was added at final concentration of 300 μg/ml, 1.5 μg/ml respectively. The medium was changed every 3 to 4 days until colonies of drug-resistant cells formed (12 to 15 days). Colonies were stained with 0.02% neutral red. Pseudovirus generated by COS-1 were incubated L929 cells and selected with drugs for about 2 weeks. Since pseudovirus without env protein or drug resistant gene carrying pseudotype virus still produced colonies, the number of colonies induced pseudotype virus without env was subtracted from the number of colonies induced by env-carrying pseudovirus.

9.2. Results

The presence of colonies indicates effective penetration, reverse transcription and integration of pseudovirus. The number of selected colonies were subtracted by the number of colonies post infected with pseudovirus without-env proteins as a background. See Table 1. As expected mouse cells (L929) expressing human topo I produced much higher number of colonies after infection with HIV pseudovirus than mouse cells not expressing topo I.

After transfecting the HIV-hyg or HIV-bsd and the pSR-E-MLV-env plasmids in COS-1 cells, the expression of the HIV gag protein was determined by immunoblot analysis. When HIV-hyg or HIV-bsd were co-transfected with pSR-E-MLV-env, bands corresponding to the processed (p24) and precursor (p55) of HIV I gag was observed. These results indicate that once the HIV virus is internalized by mouse cells expressing human topo I, the human topo I is sufficient to support HIV replication.

TABLE I

| Selected Colonies<br>Infected Cells | pNLhyg./E-pNLhyg. | PNLBS/E-pNLBS |
| --- | --- | --- |
| L929/Vector | 0–20 | 0–10 |
| L929/htopo I | 250 | 150 |

10. EXAMPLE

Screening for Inhibitors of Topo I as Anti-HIV Agents in Murine Cells

The transgenic mice and mouse cell lines expressing human topo I have utility in screening for agents that target human topo I and as a result inhibit the HIV-1 life cycle. The following example demonstrates the utility of mouse cell lines expressing human topo I in screening topo I inhibitors for their ability to inhibit HIV-1 infection. Topo I specific inhibitors, camptothecin (CPT) and TAN134A, are provided as an example of compounds to be tested for anti-HIV activity. These topo I inhibitors were analyzed for their effect on HIV reverse transcriptase activity.

10.1. Materials and Methods

MT2 cells were incubated for 2 hours with HIV-1 IIIB strain (Ratner et al., 1985 Nature 313: 277–284) at 0.1 m.o.i. with drugs. Concentrations ranged from no drugs 0,0, AZT 0.01, 0.1, 1, 10 μg/mi, CPT 0.01, 0. 1, 1 μg/ml TAN 0.01, 0. 1, 1 μg/ml, CPT 0.1, 1, 10 μg/ml, TAN 0.1, 1, 10 μg/mi respectively (FIG. 5). After washing with PBS 3 times, cells were incubated again for 72 hrs with or without concentration of drugs as indicated, then lysed with 1% SDS, 10 Mm Tris HCl (pH 8.0), 5 Mm EDTA, 1M NaCl(Hirt's method. Following overnight incubation at 4 C., large molecule of DNA were precipitated by centrifugation. Supernatants were treated with 100 μg/ml of protease K at 56° C. for 2 hrs and after treated with phenol-chloroform, small molecules of DNA were precipitated and subjected to southern hybridization. Transferred nylon membrane (Schleicher & Schuell) were probed with ($\alpha$-$^{32}$P) dCTP-random-primed-labeled primer.

10.2. Results

The presence of CPT or TAN134A reduced HIV-replication in HIV-infected cells, as shown by Southern blot analysis (FIG. 5). However, TA134A had a much more dramatic effect of reducing HIV-replication than CPT. Therefore, this example demonstrates how topoisomerase I inhibitors can be screened for their ability to inhibit the HIV life cycle.

11. EXAMPLE

Transgenic Mice Expressing Both Human CD4 and Human Topo I

The following example demonstrates the successful generation of transgenic mice expressing both human CD4 and human topo I.

Procedure

Fertilized eggs at early pronuclear stage, the male and female pronuclei being distinguished within the cytoplasm, were collected from the oviducts of C57 Black 6 female mice which had been mated to CBA males. Pooled zygotes were washed in fresh culture medium and stored until micromanipulation. The technique of microinjection is known to those skilled in the art and is described in U.S. Pat. No. 4,873,191, incorporated herein by reference.

The plasmid expressing human topo I was prepared as follows: human topo I was expressed under a granzyme B promoter which allows expression of topo I in peripheral blood cells and in particular NK cells and T lymphocytes. The plasmid containing the granzyme B promoter (Wargnier et al., 1995, Mol. Cell. Biol. 92:6930–6934) is derived from pUC19 and is called p687. The human topo I fragment was amplified by PCR techniques, using PCR primers corresponding to the sites of the topo I fragment, the Bgl II and Bam HI.

The human topo I fragment was inserted at the Bam HI/Bgl II site of p687 (FIG. 12).

The plasmid expressing human CD4 was prepared as follows: human CD4 was subcloned from plasmid pKS481/huCD4. The Bam HI to Bam HI fragment was prepared by PCR amplification. The human CD4 fragment was inserted at the BamHI site of p687.

Both plasmids were linearized by digestion with Sal I prior to microinjection. The concentration of DNA used for microinjection was 250 ng/ml.

After microinjection of the zygotes, there were five transfers of one cell eggs into five surrogate mothers, twenty seven, twenty, twenty, twenty and nineteen eggs. On the following day, there were three transfers of two cell embryos into three surrogate mothers, nineteen, eighteen and eighteen embryos. Eleven pups were born. Of the eleven pups six pups tested positive for expression of both the human CD4 and human topo I.

Transgenic mice expressing both human topo I and human CD4 were generated by expressing human topo I and CD4 under a lck promoter (Allen et al. 1992, Mol. Cell. Biol. 12:2758–68; Wildin et al. 1995, J. Immunol. 155:1286–1295) which allows expression in peripheral CD4 T lymphocytes. The plasmid plck-hGH contains the lck promoter (FIG. 13). The Bam HI/Bgl II fragment of the htopo I sequence (as described in FIG. 11) was inserted at the Bam HI site of plck-hGH. The hCD4 DNA was prepared by PCR amplification and inserted at the Bam HI site of plck-hGH.

A number of references have been cited and the entire disclosures of which are incorporated herein by reference.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A mouse cell line which expresses a heterologous gene encoding human topoisomerase I, wherein expression of said gene facilitates the replication of an HIV pseudovirion containing a heterologous glycoprotein, wherein said glycoprotein serves to facilitate the entry of psuedovirions into said cells.

2. A mouse cell line which co-expresses heterologous genes encoding human topoiserase I and human CD4 wherein co-expression of said genes facilitates the entry and replication of HIV in said mouse cells.

3. A method for identifying test compounds capable of inhibiting HIV infection, by (a) administering said test compound to the mouse cell line of claim 1; (b) infecting the cells with as HIV pseudovirus; and (c) measuring HIV replication.

4. A method for identifying test compounds capable of inhibiting HIV infection, by (a) administering said test compound to the mouse cell line of claim 2; (b) infecting the cells with HIV; and (c) measuring HIV replication.

* * * * *